(12) United States Patent
Yeh

(10) Patent No.: US 12,320,984 B2
(45) Date of Patent: *Jun. 3, 2025

(54) HEAD WEARABLE VIRTUAL IMAGE MODULE FOR SUPERIMPOSING VIRTUAL IMAGE ON REAL-TIME IMAGE

(71) Applicant: HES IP HOLDINGS, LLC, Austin, TX (US)

(72) Inventor: Feng-Chun Yeh, Taipei (TW)

(73) Assignee: Oomii Inc., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 18/890,584

(22) Filed: Sep. 19, 2024

(65) Prior Publication Data

US 2025/0013054 A1    Jan. 9, 2025

Related U.S. Application Data

(63) Continuation-in-part of application No. 18/510,258, filed on Nov. 15, 2023, now Pat. No. 12,099,200, (Continued)

(51) Int. Cl.
*G09G 3/00* (2006.01)
*A61B 90/00* (2016.01)
*G02B 27/01* (2006.01)

(52) U.S. Cl.
CPC .......... *G02B 27/0172* (2013.01); *A61B 90/37* (2016.02); *G09G 3/001* (2013.01); (Continued)

(58) Field of Classification Search
CPC .............. A61B 2090/365; A61B 90/37; G02B 2027/0138; G02B 2027/014; (Continued)

(56) References Cited

U.S. PATENT DOCUMENTS 10,429,941 B2  10/2019  Kamoda
10,467,770 B2  11/2019  Sato et al.
(Continued)

FOREIGN PATENT DOCUMENTS

CN    101862178 A    10/2010
CN    102750418 A    10/2012
(Continued)

OTHER PUBLICATIONS

Taiwanese Office Action, dated Nov. 22, 2024, in a counterpart Taiwanese patent application, No. TW 113135710.
(Continued)

*Primary Examiner* — Insa Sadio
(74) *Attorney, Agent, or Firm* — Chen Yoshimura LLP

(57) ABSTRACT

Disclosed is a system for superimposing a virtual image on a real-time image or real object. The system comprises a right collimated light signal generator for generating a right collimated light signal and a left collimated light signal generator for generating a left collimated light signal corresponding to the right collimated light signal which is directed towards the other retina of the viewer; wherein the right collimated light signal and the left collimated light signal form a binocular pixel of a virtual image with a first depth, the first depth which the viewer perceives is modified by changing a convergence angle between light path extensions of the right collimated light signal and the corresponding left collimated light signal projected into the viewer's eyes based on an interpupillary distance, the first depth corresponds to a depth location of a converging point of light path extensions of the right collimated light signal and the corresponding left collimated light signal.

8 Claims, 18 Drawing Sheets

Related U.S. Application Data which is a continuation of application No. 18/331,910, filed on Jun. 8, 2023, now Pat. No. 11,822,089, which is a continuation of application No. 17/623,260, filed as application No. PCT/US2021/046078 on Aug. 16, 2021, now Pat. No. 11,698,535.

(60) Provisional application No. 63/085,172, filed on Sep. 30, 2020, provisional application No. 63/065,506, filed on Aug. 14, 2020.

(52) U.S. Cl.
CPC .. *A61B 2090/365* (2016.02); *G02B 2027/014* (2013.01); *G09G 2320/0693* (2013.01); *G09G 2340/12* (2013.01); *G09G 2354/00* (2013.01); *G09G 2380/08* (2013.01)

(58) Field of Classification Search
CPC .............. G02B 26/0833; G02B 27/017; G02B 27/0172; G06F 3/147; G09G 2320/0693; G09G 2340/04; G09G 2340/12; G09G 2354/00; G09G 2380/08; G09G 3/001
See application file for complete search history.

(56) References Cited

U.S. PATENT DOCUMENTS

| | | | |
|---|---|---|---|
| 10,510,137 | B1 | 12/2019 | Kitain et al. |
| 10,517,544 | B2 | 12/2019 | Taguchi et al. |
| 10,706,600 | B1 | 7/2020 | Yoon et al. |
| 2012/0050269 | A1 | 3/2012 | Awaji |
| 2013/0135295 | A1 | 5/2013 | Li et al. |
| 2014/0211289 | A1 | 7/2014 | Hino et al. |
| 2016/0033771 | A1 | 2/2016 | Tremblay et al. |
| 2016/0234482 | A1 | 8/2016 | Bickerstaff et al. |
| 2016/0284129 | A1 | 9/2016 | Nishizawa et al. |
| 2017/0027651 | A1 | 2/2017 | Esterberg |
| 2017/0068091 | A1* | 3/2017 | Greenberg ........... G02B 26/101 |
| 2017/0090202 | A1 | 3/2017 | Tatsuta |
| 2017/0285343 | A1 | 10/2017 | Belenkii et al. |
| 2018/0140260 | A1 | 5/2018 | Taguchi et al. |
| 2018/0249150 | A1 | 8/2018 | Takeda et al. |
| 2018/0262758 | A1* | 9/2018 | El-Ghoroury ........ G02B 27/017 |
| 2019/0281279 | A1 | 9/2019 | Peuhkurinen et al. |
| 2019/0384065 | A1 | 12/2019 | Shau et al. |
| 2020/0138518 | A1 | 5/2020 | Lang |
| 2021/0003848 | A1 | 1/2021 | Choi et al. |
| 2021/0055555 | A1 | 2/2021 | Chi et al. |
| 2022/0146839 | A1 | 5/2022 | Miller |

FOREIGN PATENT DOCUMENTS

| | | |
|---|---|---|
| CN | 103119512 A | 5/2013 |
| CN | 104010561 A | 8/2014 |
| CN | 204807808 U | 11/2015 |
| CN | 105527710 B | 4/2016 |
| CN | 106909222 A | 6/2017 |
| CN | 107016685 A | 8/2017 |
| EP | 3388921 A1 | 10/2018 |
| JP | 2013-211308 A | 10/2013 |
| JP | 2014-130204 A | 7/2014 |
| JP | 2017-049468 A | 3/2017 |
| JP | 2018-137505 A | 8/2018 |
| TW | I544447 B | 8/2016 |
| TW | I692348 B | 5/2020 |
| WO | 2018/175265 A1 | 9/2018 |
| WO | 2022/036302 A1 | 2/2022 |

OTHER PUBLICATIONS

PCT/US2021/046078 Isr and Written Opinion mailed issued on Nov. 24, 2021.
PCT/US2021/046078 International Preliminary Report issued on Dec. 16, 2022.
Cn 202180004252.X Office Action issued on Apr. 18, 2024.
EP 21827555.0 European Search Report issued on Aug. 8, 2023.
JP 2022-503559 Office Action issued on Feb. 20, 2024.
JP 2022-503559 Office Action issued on Sep. 10, 2024.
TW 110130182 Office Actioin issued on Dec. 15, 2024.
U.S. Appl. No. 18/510,258, Non-final Office Action issued on Jun. 6, 2024.

* cited by examiner

| Virtual binocular pixel | Pair of right pixel and left pixel | Address pointer |
|---|---|---|
| VBP(1) | RRI(1,1) & LRI(1,1) [R11 & L11] | Memory address 1 |
| VBP(2) | RRI(2,1) & LRI(1,1) [R21 & L11] | Memory address 2 |
| ... | ... | ... |
| VBP(7) | RRI(1,1) & LRI(2,1) [R11 & L21] | Memory address 7 |
| ... | ... | ... |
| VBP(37) | RRI(1,2) & LRI(1,2) [R12 & L12] | Memory address 37 |
| ... | ... | ... |
| VBP(216) | RRI(6,6) & LRI(6,6) [R66 & L66] | Memory address 216 |

FIG. 12

HEAD WEARABLE VIRTUAL IMAGE MODULE FOR SUPERIMPOSING VIRTUAL IMAGE ON REAL-TIME IMAGE

BACKGROUND OF THE INVENTION

Field of the Invention

The present disclosure relates generally to methods and systems for superimposing a virtual image on a real-time image and, in particular, to methods and systems for superimposing a virtual image with depths, which is generated by projecting multiple right collimated light signals and corresponding left lights signals to a viewer's eyes, on a real-time image.

Description of Related Art

Many visualization assistance systems and methods for aiding medical practitioners during medical exams or surgeries, including ophthalmic surgery, have been developed in recent years. During a medical procedure, the visualization assistance systems can provide additional visual information of the patients, such as medical records, operation parameters such as photograph, magnetic resonance imaging (MRI), x-ray, computed tomography (CT), or optical coherence tomography (OCT) . . . etc. In some cases, the additional visual information is a processed image of the patient, such as CT image with some marks. The visualization assistance systems are often used together with other medical instruments capable of providing real-time images of the patients. The medical practitioner may receive the additional information provided by the visualization assistance systems, separated from the real-time images. For example, the additional information is separately displayed by a monitor, instead of from a surgical microscope where the real-time image of the patent can be observed. The monitor usually can only provide a two-dimensional image. However, during medical procedures, the medical practitioner desire to observe the additional visual information (e.g. previously processed image of the patient) overlapped with the real-time image of the patient. In addition, conventional visualization assistance systems can only provide the additional visual information in a 2D image. Thus, the ability to produce three-dimensional images for additional visual information overlapped with the real-time images of the patient becomes a main interest of the medical industry. For example, in an ophthalmic exam or surgery, the medical practitioner operates by looking through the eyepieces of an ophthalmic microscope, thus viewing the real-time optical images of the patient's eye. However, the surgeon cannot observe a processed retinal image of the patient's eye at the same time through the microscope during the procedure and has to turn his/her head to observe a separate monitor and then back to the microscope. Therefore, there remains a need for incorporating additional visual information of the patient given by the visualization assistance systems with the real-time optical images viewed by the medical practitioner.

SUMMARY

An object of the present disclosure is to provide a system and a method for superimposing a virtual image on a real-time image. A system for superimposing a virtual image on a real-time image or real object comprises a real-time image module and a virtual image module. The real-time image module comprises a magnification assembly to generate a real-time image of an object at a first location and a first depth, with a predetermined magnification.

The virtual image module generates a virtual image by respectively projecting a right collimated light signal to a viewer's right eye and a corresponding left collimated light signal to a viewer's left eye. The right collimated light signal and the corresponding left collimated light signal are perceived by the viewer to display the virtual image at a second location and a second depth. The second depth is related to an angle between the right collimated light signal and the corresponding left collimated light signal projected to the viewer's eyes. In one embodiment, the second depth is approximately the same as the first depth. The virtual image is superimposed on the real-time image to provide the viewer more information. Thus, in one embodiment, the virtual image is a processed image of the real object.

The magnification of the real-time image is adjustable. After the real-time image is magnified, the virtual image may be manually or automatically magnified to maintain the original superimposition between the virtual image and the real-time image. An automatic mode for superimposition may be selected.

In order to superimpose the virtual image on the real-time image, the system has to be calibrated first for the viewer. Because every viewer's eyes have different physical characteristics, including interpupillary distance, the system has to be calibrated specifically for the viewer to assure that with the right collimated light signals and left collimated light signals projected into the viewer's eyes, the viewer would perceive the virtual image displayed at the second location and the second depth.

The process of superimposing a virtual image on a real-time image includes (a) selecting a first point on the real-time image as a first landmark, (b) displaying the real-time image at a first location and a first depth with a predetermined magnification, (c) projecting a virtual image by respectively projecting a right collimated light signal to a viewer's right eye and a corresponding left collimated light signal to a viewer's left eye for the viewer to perceive the virtual image at a second location and a second depth so that the corresponding first landmark on the virtual image overlaps the first landmark on the real-time image. In one embodiment, the depth of the first landmark on the real-time image is approximately the same as the depth of the corresponding first landmark on the virtual image. To have more precise superimposition, a second landmark or a third landmark may be used in a similar manner.

Additional features and advantages of the disclosure will be set forth in the descriptions that follow, and in part will be apparent from the descriptions, or may be learned by practice of the disclosure. The real objectives and other advantages of the disclosure will be realized and attained by the structure and method particularly pointed out in the written description and claims thereof as well as the appended drawings. It is to be understood that both the foregoing general description and the following detailed description are exemplary and explanatory and are intended to provide further explanation of the invention as claimed.

BRIEF DESCRIPTION OF THE DRAWINGS

FIG. 12 is a table illustrating an embodiment of a look up table in accordance with the present invention.

DETAILED DESCRIPTION OF PREFERRED EMBODIMENTS

Figure 1A:
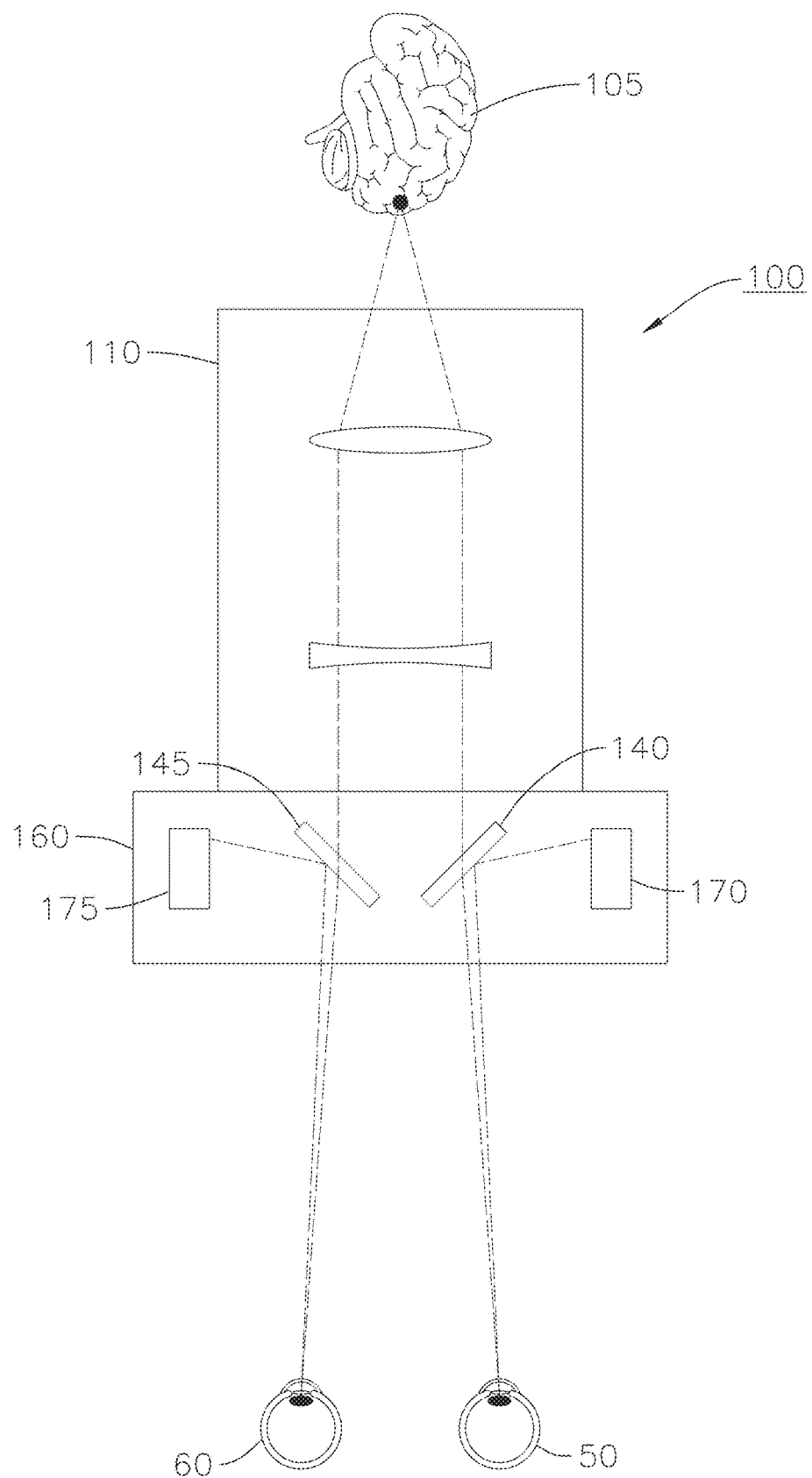
FIG. 1A is a schematic diagram illustrating an embodiment of a system in accordance with the present invention.

The terminology used in the description presented below is intended to be interpreted in its broadest reasonable manner, even though it is used in conjunction with a detailed description of certain specific embodiments of the technology. Certain terms may even be emphasized below; however, any terminology intended to be interpreted in any restricted manner will be specifically defined as such in this Detailed Description section.

The present invention relates to systems and methods for superimposing a virtual image on a real-time image or real object. A virtual image with a depth may be superimposed on a real-time image or real object to provide a viewer more information in connection with the real-time image or real object, such as surgery guidance, instructions, navigation etc. The real-time image is an image that reflects changes of the real object in a real-time manner. The real-time image may be a two-dimensional (2D) image or a three-dimensional (3D) image. In one embodiment, the real-time image is generated by lights reflected or emitted from the real object, for example, the image observed by a microscope or a telescope. In some embodiments, the real-time image may be reflected or emitted from the real object and observed by the eye without the present of microscope or telescope. In another embodiment, the real-time image is generated by a display which receives an image of an object possibly taken by a camera in a real-time manner, for example, the image on a display from an endoscope. In addition, the real-time image may be a real image or a virtual image. The virtual image with a depth is generated by projecting light signals to the viewer's both eyes. The depth of the virtual image is related to an angle between the right collimated light signal and the corresponding left collimated light signal projected to the viewer's eyes. The virtual image may be a 2D image or a 3D image. When the virtual image is superimposed on the real-time image or real object, a portion of the virtual image is overlapped with the real-time image.

A system for superimposing a virtual image on a real-time image or real object comprises a real-time image module and a virtual image module. In general, the real-time image module may comprise any optical elements with light reflective, penetrative, or refractive properties. The viewer can observe the real-time image of a real object at a second location with a second depth. In some embodiments, the real-time image module may comprise a magnification assembly to magnify a real-time image of the real object at a second location and a second depth, with a predetermined magnification. The magnification is a process of enlarging the apparent size, not physical size, of an object. This enlargement is quantified by a calculated number also called "magnification," the ratio between the apparent (real-time image) size of an object and the observed size of the real object without the magnification. The magnification is adjustable and may be any positive number such as 0.5, 1, and 10. When the magnification is less than one, it refers to a reduction in size, sometimes called minification or de-magnification.

The virtual image module generates a virtual image by respectively projecting a right collimated light signal to a viewer's right eye and a corresponding left collimated light signal to a viewer's left eye. The right collimated light signal and the corresponding left collimated light signal are perceived by the viewer to display the virtual image at a first location and a first depth. The first depth is related to an angle between the right collimated light signal and the corresponding left collimated light signal projected to the viewer's eyes. In one embodiment, the first depth is approximately the same as the second depth.

The virtual image is superimposed on the real-time image or real object to provide the viewer with more information. Thus, in one embodiment, the virtual image is a processed image of the real object. For example, the real object may be a brain and the real-time image is the brain image generated or processed in a real-time manner. However, in some embodiments, the viewer may view the image real object directly (e.g., without magnification, or the image of the real object viewed by the viewer is not captured and reproduced by photo-sensing device and displaying device in any manner). If the viewer views the real object directly, the viewer may see the virtual image being superimposed directly on the real object. The virtual image may be the CT or MRI image of the brain taken before the surgery and is marked with the location of brain tumor to be removed in the surgery. The marked virtual image is superimposed on the real-time image of the brain or the brain during the surgery to assist a surgeon identifying the location of the brain tumor to be removed. In this circumstance, to be accurate on the surgery location, the first depth of the virtual image (marked CT or MRI image) is approximately the same as the second depth of the real-time image or real object, the actual brain from a surgical microscope. The virtual image may further include some text information, marks, and pointers for guidance or explanation to assist diagnosis and treatment. In addition, the image superposition may allow the viewer to compare previous image of the real object presented by the virtual image and the current status of the real object presented by the real-time image and thus to estimate disease progression and treatment results.

The magnification of the real-time image is adjustable. In one embodiment, such adjustment can be achieved manually by rotating a knob, changing an objective lens, controlling a virtual switch, or giving an oral instruction. After the real-time image is magnified, the virtual image may be manually or automatically magnified to maintain the original superimposition between the virtual image and the real-time image. An automatic mode for superimposition may be selected.

In order to superimpose the virtual image on the real-time image or real object, the system has to be calibrated first for the viewer. Because every viewer's eyes have different physical characteristics, including interpupillary distance (IPD), the system has to be calibrated specifically for the viewer to assure that with the right collimated light signals and left collimated light signals projected into the viewer's eyes, the viewer would perceive the virtual image displayed at the second location and the second depth. For example, the distance between the right eyepiece and the left eyepiece of a microscope needs to be adjusted to fit the viewer's interpupillary distance; the angles between the right collimated light signals and the corresponding left collimated light signals need to be adjusted so that the virtual image is perceived by the viewer at exactly the second depth.

The process of superimposing a virtual image on a real-time image includes (a) selecting a first point of a real-time image as a first landmark, (b) displaying a real-time image at a second location and a second depth with a predetermined magnification, (c) projecting a virtual image by respectively projecting a right collimated light signal to a viewer's right eye and a corresponding left collimated light signal to a viewer's left eye for the viewer to perceive the virtual image at a first location and a first depth so that the corresponding first landmark on the virtual image overlaps the first landmark on the real-time image. As described above, the first depth is related to an angle between the right collimated light signal and the corresponding left collimated light signal projected to the viewer's eyes. In one embodiment, the depth of the first landmark on the real-time image is approximately the same as the depth of the corresponding first landmark on the virtual image. To have more precise superimposition, a second landmark or a third landmark may be used in a similar manner.

The process of superimposing a virtual image on a real object includes (a) selecting a first point of a real object as a first landmark, (b) projecting a virtual image by respectively projecting a right collimated light signal to a viewer's right eye and a corresponding left collimated light signal to a viewer's left eye for the viewer to perceive the virtual image at a first location and a first depth so that the corresponding first landmark on the virtual image overlaps the first landmark on the real object. As described above, the first depth is related to an angle between the right collimated light signal and the corresponding left collimated light signal projected to the viewer's eyes. In one embodiment, the depth of the first landmark on the real object is approximately the same as the depth of the corresponding first landmark on the virtual image. To have more precise superimposition, a second landmark or a third landmark may be used in a similar manner.

Figure 1B:
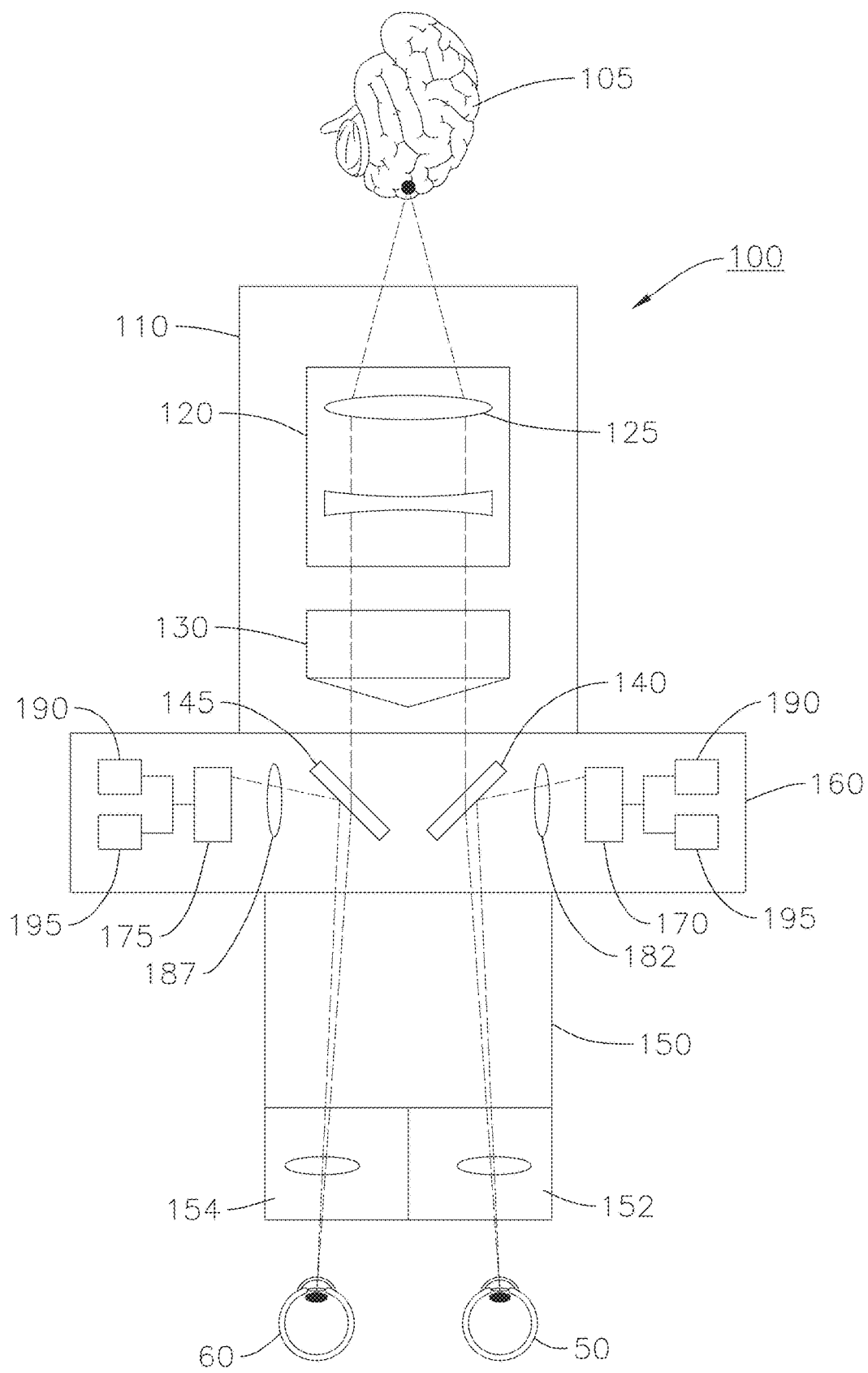
FIG. 1B is a schematic diagram illustrating another embodiment of a system in accordance with the present invention.

As shown in FIGS. 1A&1B, a system 100 for imposing a virtual image 165 on a real-time image 115 includes a real-time image module 110 and a virtual image module 160. The real-time image module 110 may include a magnification assembly 120 to generate a magnified real-time image of an object 105, such as a brain, for both eyes of a viewer. The magnification assembly 120 may include multiple optical units and assemblies, such as various types of lenses, including objective lens 113. In another embodiment, the magnification assembly 120 may use electronic circuits to process and magnify the real-time image of the real object 105. The magnification of the real-time image module may be determined before observation and adjustable during the observation. The magnification may be ½, 1, 3, 10, 100, etc. The magnification adjustment may be performed via a user interface in communication with the real-time image module. The real-time image module may have one set of optical units and assemblies to generate the real-time image for both eyes of the viewer or two separate sets of optical units and assemblies to respectively generate the real-time image for the right eye and the left eye of the viewer. The real-time image module 110 may further include a prism assembly 130 to redirect the direction of lights, beam splitters 140, 145 to split the lights, an observation tube 150 to guide the lights, and eyepieces 152, 154 to further magnify the image. Again, the real-time image may be generated from the lights reflected or emitted from the real object 105, such as the real-time image generated by a microscope, including a surgical microscope. In another embodiment, the real-time image may be generated by an image catching device and a display device, such as an endoscope and its associated display. Depending on the image size and resolution, the real-time image may actually or conceptually contain 921, 600 pixels in a 1280×720 array. Each pixel may have a slightly different location and depth from its adjacent pixel. A representative pixel, such as a first landmark, may be selected for the real-time image. A landmark, such as the first landmark and the second landmark, is usually a unique point with a distinguishable feature that may be easily recognized by the viewer in the real-time image, such as the central point, the intersection of two specific blood vessels. A landmark may be a pixel or comprise multiple pixels adjacent to each other. In one embodiment, the location and the depth of the representative pixel may be used for those of the real-time image—the second location and the second depth.

The virtual image module 160, configured to be connected with the real-time image module 110, includes a right collimated light signal generator 170 and a left collimated light signal generator 175. The right collimated light signal generator 170 generates multiple right collimated light signals for a virtual image and is likely located closely to right portion of the real-time image module. Similarly, the left collimated light signal generator 175 generates multiple left collimated light signals for a virtual image and is likely located closely to left portion of the real-time image module. The right collimated light signals are then redirected by the right beam splitter 140 towards one eye of the viewer. Similarly, the left collimated light signals are then redirected by the left beam splitter 145 towards the other eye of the viewer. The redirected right collimated light signals and corresponding redirected left collimated light signals are perceived by the viewer to display the virtual image at a second depth. Depending on the image size and resolution, the virtual image may actually contain 921,600 virtual binocular pixels in a 1280×720 array. Each virtual binocular pixel may have a slightly different location and depth from its adjacent pixel. A representative virtual binocular pixel, such as a first landmark, may be selected for the virtual image. In one embodiment, the location and the depth of the representative virtual binocular pixel may be used for the virtual image—the second location and the second depth. After the viewer's eyes receiving a redirected right collimated light signal and a corresponding redirected left collimated light signal of the representative virtual binocular pixel, the viewer perceives the representative virtual binocular pixel at the second depth that is related to an angle between such redirected right collimated light signal and the corresponding redirected left collimated light signal.

The light beams of the real-time image may also pass through the right beam splitter 140 and the left beam splitter 145 towards the viewer's eyes. Thus, to certain extent, the right beam splitter 140 and the left beam splitter 145 are shared by both the real-time image module and the virtual image module. In one embodiment, the beam splitters originally installed in the real-time image module to share the real-time image with other viewers can be rotated by an appropriate angle for redirecting light signals generated from the virtual image module toward the viewer's eyes.

Figure 1C:
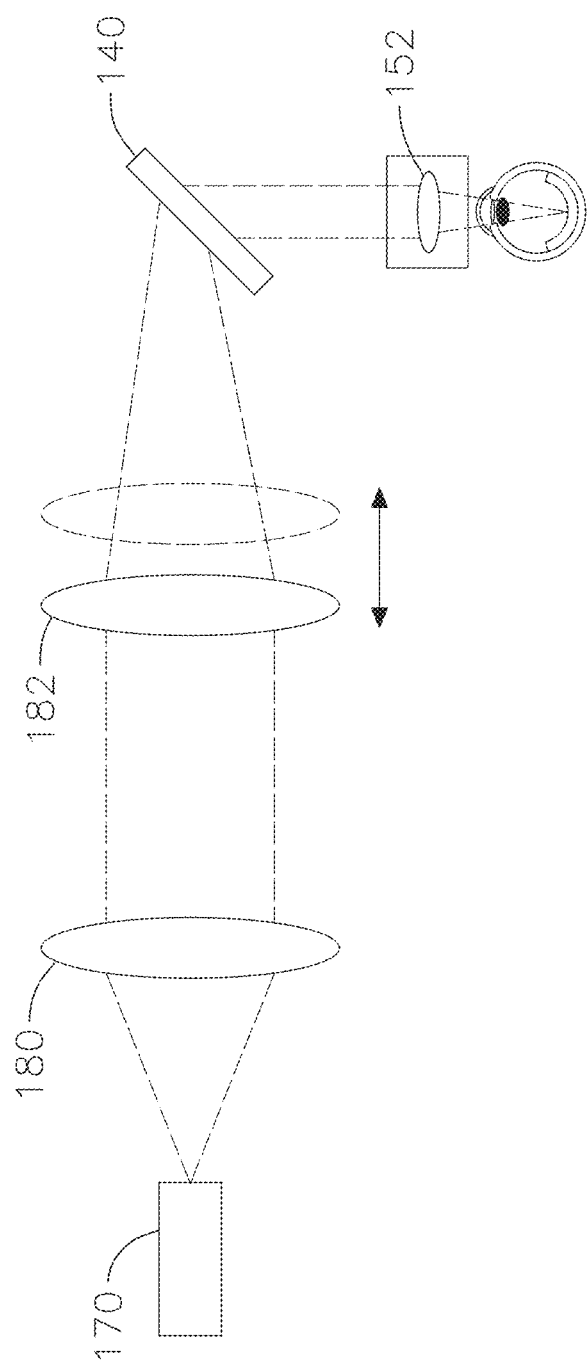
FIG. 1C is a schematic diagram illustrating a collimator in a virtual image module of a system in accordance with the present invention.

As shown in FIGS. 1B and 1C, the virtual image module 160 may further include a right focus adjustment unit 182 between the right collimated light signal generator 170 (or the right collimator 180 if available) and right beam splitter 140 and a left focus adjustment unit 187 between the left collimated light signal generator 175 (or the right collimator 185 if available) and the left beam splitter 145 to improve clarity of the virtual image for the viewer. The right/left focus adjustment unit may include optical units such as various types of lens, including convex lens. In one embodiment where a convex lens is used for the focus adjustment unit, adjusting its distance with the light signal generator would change the focus location of the light beams, assuming the distance between the light signal generator and the beam splitter remains the same. The closer the focus location of the light beams is to the retina, the clear the virtual image is for the viewer. Since the axial length of viewers' eyes may vary, the preferred focus location of light beams and, thus, the distance between the light signal generator and the focus adjustment unit vary accordingly. In other words, for the viewer with longer axial length, the focus adjustment unit needs to be more far away from the light signal generator so that the focus location of the light beams is closer to the viewer's retina. When the collimator is available, the focus adjustment unit is positioned between the collimator and the beam splitter. After passing through the collimator, the light beams from the light signal generator become substantially parallel and then converge after passing through the focus adjustment unit. In addition, since the focus adjustment unit does not alter the incident angle of light beams, the depth of the virtual image would be unaffected.

As partly shown in FIG. 1C, the virtual image module 160 may further include a right collimator 180 and a left collimator 185 to narrow the light beam of the multiple light signals, for example to cause the directions of motion to become more aligned in a specific direction or to cause spatial cross section of the light beam to become smaller. The right collimator 180 may be positioned between the right collimated light signal generator 170 and the right beam splitter 140 and the left collimator 185 may be positioned between the left collimated light signal generator 175 and the left beam splitter 145. The collimator may be a curved mirror or lens.

In addition, the virtual image module 160 may include a control module 190 to control virtual image signals for the right collimated light signal generator 175 and the left collimated light signal generator 175. The control module 190 is communicatively connected to the virtual image module 160 to adjust the right collimated light signals and the corresponding left collimated light signals so that the virtual image may be automatically modified to superimpose the virtual image on the real-time image based on a variation of the real-time image. The variation of the real-time image includes the variation in view angle, magnification, or location. For example, when the magnification of the real-time image is adjusted such as from 3 times to 10 times, the control module 190 would process the image signals to magnify the virtual image to the same size and use at least the first landmark to cause the virtual image to continue being superimposed on the real-time image. Although the control module 190 includes one or more processors, for complicated signal processing, the control module 190 may use an external server 250 for calculations.

The virtual image may be stored in a memory module 195. In one embodiment, the virtual image is a processed image of the real object, such as an X-ray image, an ultrasound image, a CT image, and a MRI image of the real object with some marks or highlights on the area of interest. The virtual image may further include some text information and pointers for guidance or explanation. For example, the virtual image may be a previously taken and processed retinal image of a patient with marks on bleeding blood vessels to be sealed by laser. The system 100 may superimpose such a virtual image on the real-time image of the same retina from a slit-lamp microscope. The control module 190 may retrieve the virtual image stored in the memory module 195 and then generate virtual image signals for the right collimated light signal generator 170 and the left collimated light signal generator 175 whenever necessary.

Figure 2:
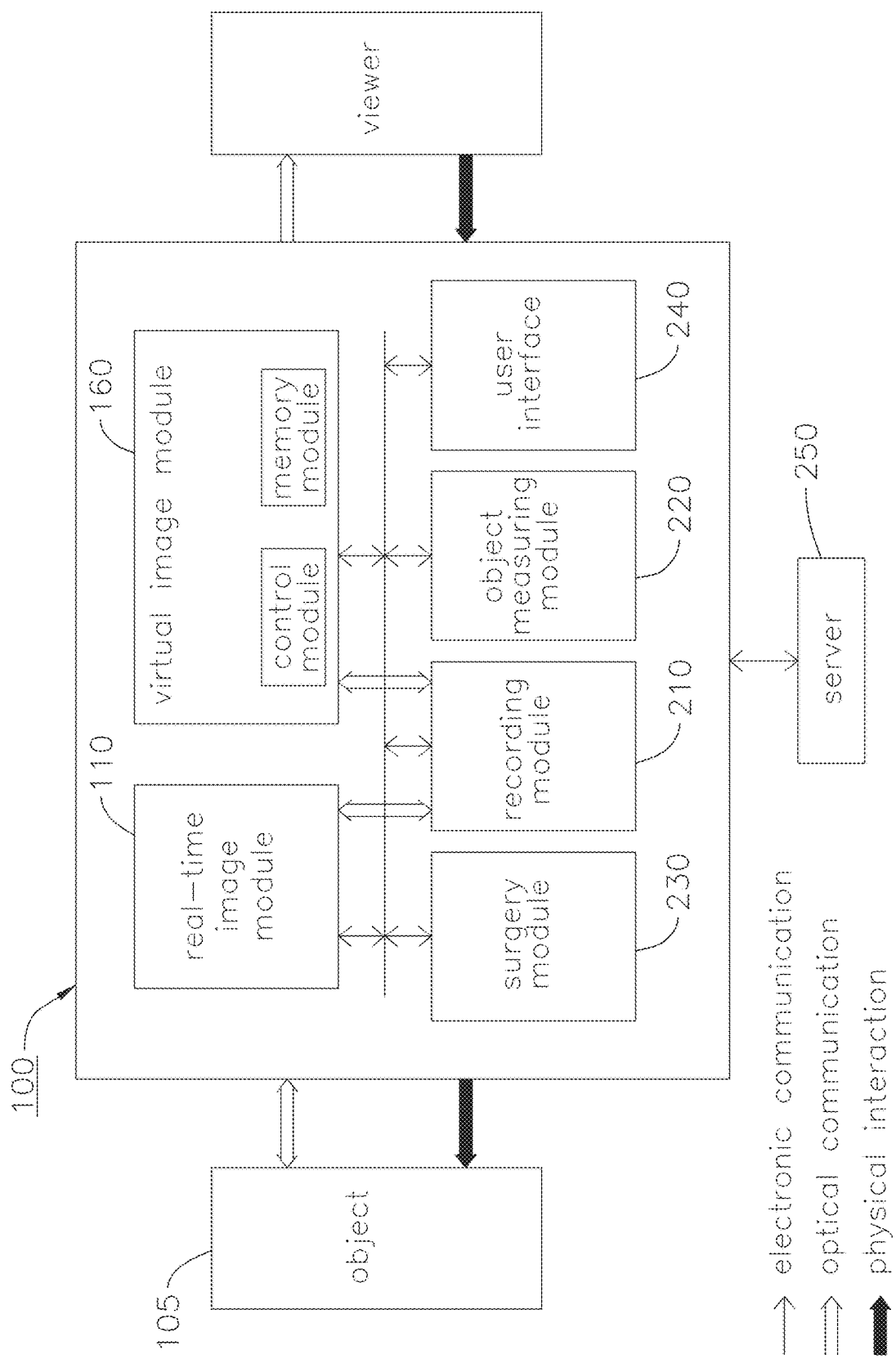
FIG. 2 is a block diagram illustrating an embodiment of a system with various modules in accordance with the present invention.

As shown in FIG. 2, in addition to the real-time image module 110 and the virtual image module 160, the system 100 may further include a recording module 210 to record either or both the real-time image and the virtual image, an object measuring module 220 to measure a location and a depth of the real object, a surgery module 230 to physically perform a surgery on the real object 105, and a user interface 240 for the viewer to communicate with various modules of the system 100 and to control various functions of the system 100. All modules of the system 100 may have electronic communication with each other via wired or wireless manner. The wireless manner may include WiFi, bluetooth, near field communication (NFC), internet, telecommunication, radio frequency (RF), etc. The real-time image module 110, the virtual image module 160, and the recording module 210 may have optical communication with each other via optical beams and optical signals. The viewer may observe the real-time image and the virtual image through the system 100 and then control the system 100 via physical interaction with the user interface 240. The system 100 may have optical communication with the real object 105 such as receiving light beams reflected or emitted from the real object, and projecting light beams on the real object. The system 100 may have physical interactions with the real object 105, such as performing a laser surgery on the real object.

As described above, the system 100 may further include a recording module 210 to record either or both of the real-time image and the virtual image. In one embodiment, the recording module 210 may be positioned between the right beam splitter 140 and the left beam splitter 145 to record the real-time image—the light beams from the real object and respectively reflected by the right beam splitter and the left beam splitter during a surgery. The recording module 210 may include a digital camera or a charge-coupled device (CCD) to capture the image. In another embodiment, the recording module 210 may be positioned adjacent to the eyepieces to record the light beams passing through the eyepieces but before arriving the viewer's eyes, including both light beams forming the real-time image and the virtual image. The recording module 210 may be connected to the control unit to directly record the virtual image signals and the associated information and parameters for future displaying.

As described above, the system 100 may further include an object measuring module 220 to measure a location and a depth of the real object. The real object measuring module 220 configured to be connected to the system may continuously or periodically measure the location and depth of the real object relative to the real object measuring module (or the viewer), and communicate the associated information to the virtual image module for adjusting the virtual image. Upon receipt of such information, the control module 190 may process the virtual image signals based on the updated location and depth of the real object relative to the real object measuring module and the viewer. As a result, the virtual image may remain superimposed on the real-time image or real object. The distance or relative location between the real object 105 and the real object measuring module 220 (or the viewer's eyes) may change along the time. In one situation, the real object 105, such as a portion of human body like eyeballs, may move during a surgery. In another situation, the system 100 may be worn by a viewer, such as a surgeon, and the viewer may move his/her head during a surgery. Thus, the relative location and distance between the real object 105 and the viewer's eye need to be measured and calculated in order to maintain the superimposition of the virtual image on the real-time image or real object. The real object measuring module 220 may include a gyroscope, indoor/outdoor global positioning system (GPS) and a distance measurement component (e.g. emitters and sensors) to precisely track the variation of such relative location and depth of the real object 105.

As described above, the system 100 may further include a surgery module 230 to physically perform a surgery on the real object 105. The surgery module 230 may include a laser to remove tissues or to seal bleeding blood vessels, and/or a scalpel to cut tissues. The surgery module 230 may coordinate with the real-time image module 110 to position the laser and/or the scalpel towards the spot of interest identified by the viewer, e.g. a surgeon, as shown in the real-time image.

As described above, the system 100 may further include a user interface 240 for the viewer to control various functions of the system 100, for example the magnification of the real-time image, the first location and the first depth of the virtual image, the focus adjustment unit, the recording module 210, the real object measuring module 220, etc. The user interface 240 may be operated by voices, hand gestures, finger/foot movements and in the form of a pedal, a keyboard, a mouse, a knob, a switch, a stylus, a button, a stick, a touch screen, etc. The user interface 240 may communicate with other modules (including the real-time image module 110, the virtual module 160, the recording module 210, the real object measuring module 220, and the surgery module 230) of the system 100 via wired or wireless manner. The wireless manner may include WiFi, bluetooth, near field communication (NFC), internet, telecommunication, radio frequency (RF), etc. The viewer may use the user interface 240, such as controlling a stick, to move a cursor to a spot of interest on the real-time image, and then use the user interface 240, such as pressing a pedal, to initiate the laser beam towards the corresponding spot of interest on the real object 105 for removing the tissue or sealing a bleeding blood vessel.

Figure 3A:
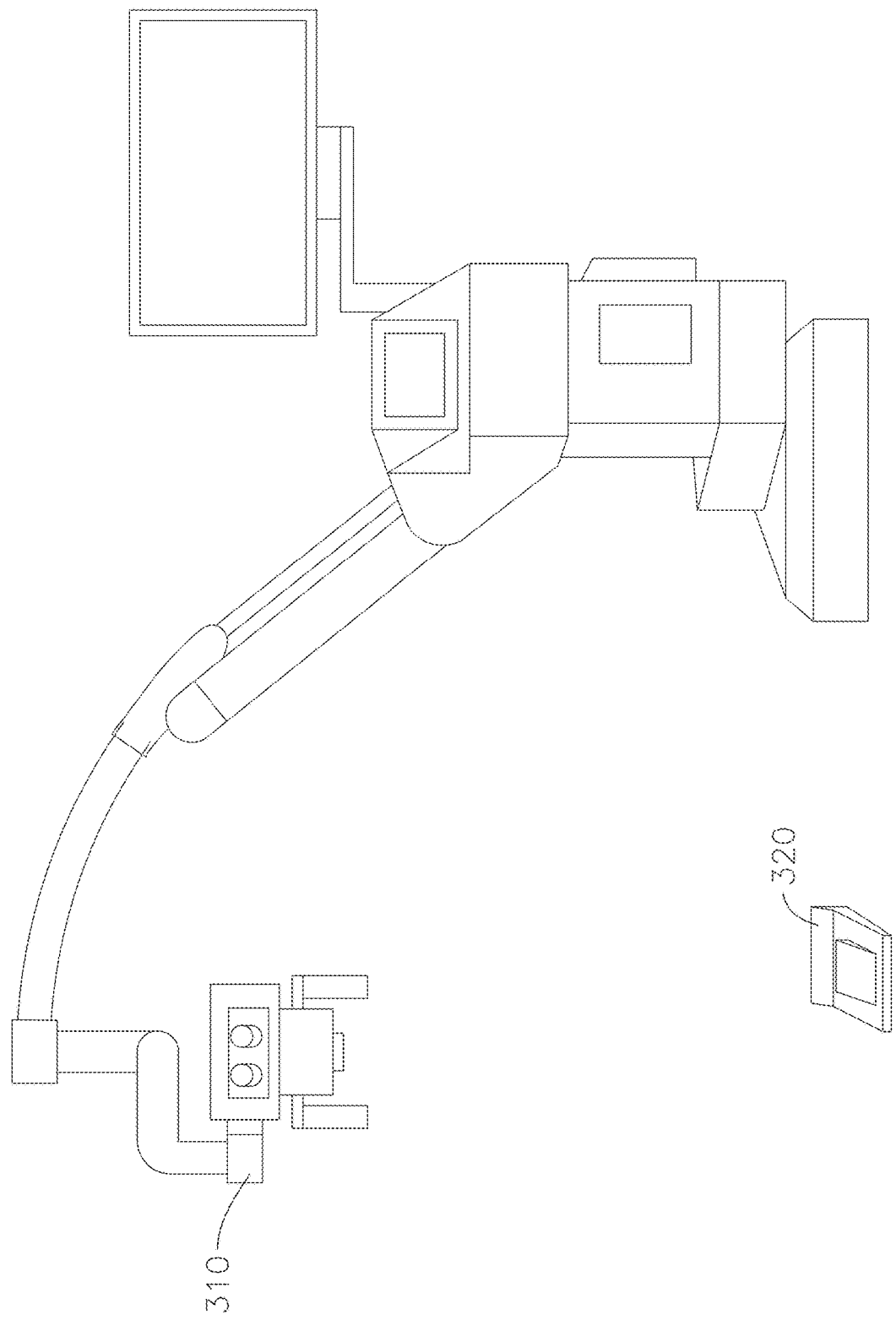
FIGS. 3A and 3B are schematic diagrams illustrating possible embodiments of a system in accordance with the present invention.

In one embodiment, the system 100 may be an AR microscope for surgery and/or diagnosis, such as an AR ophthalmoscope and an AR slit-lamp microscope. FIG. 3A shows an example of a stationary AR surgical microscope 310 which includes a user interface pedal 320.

Figure 3B:
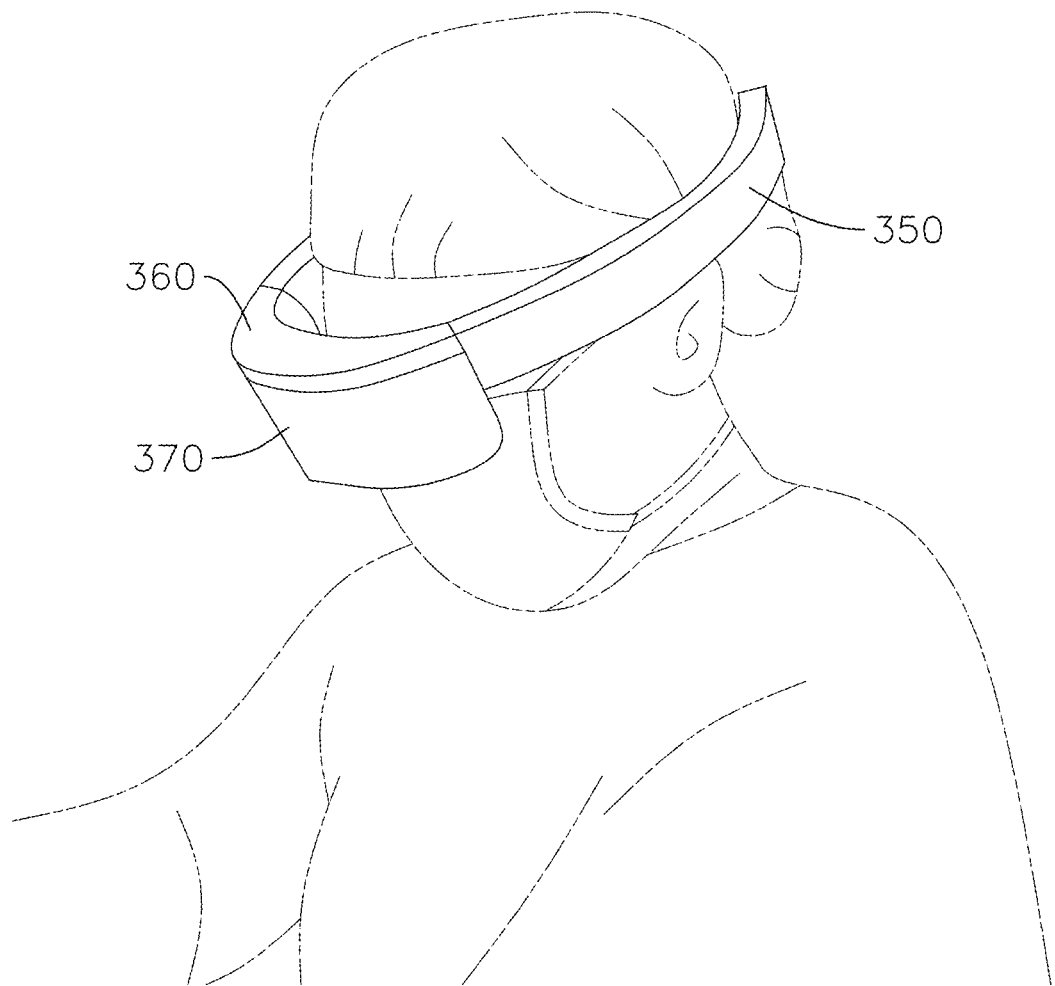
Figure 3C:
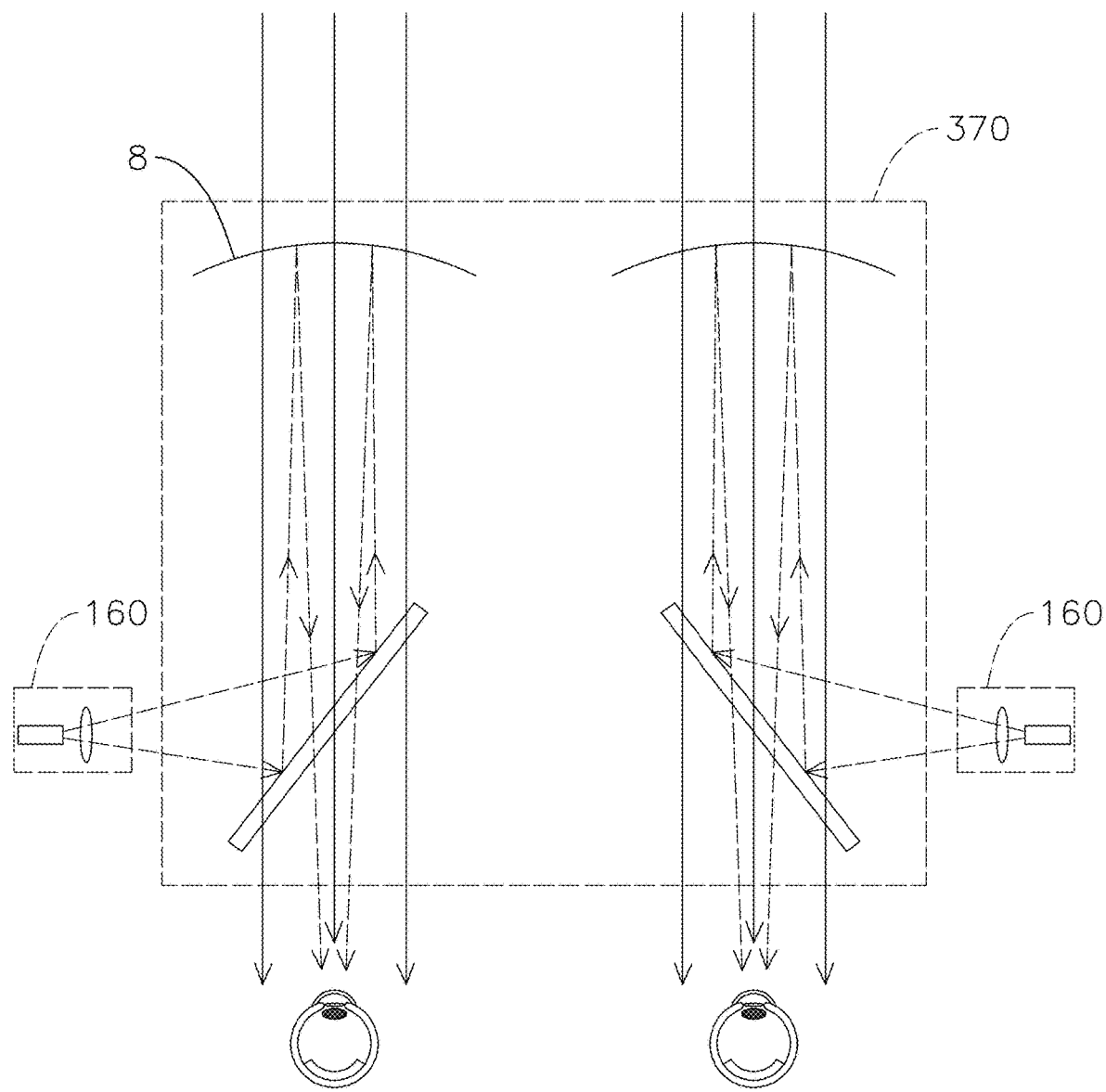
FIG. 3C is a schematic diagram illustrating an embodiment of the portable AR device.
Figure 3D:
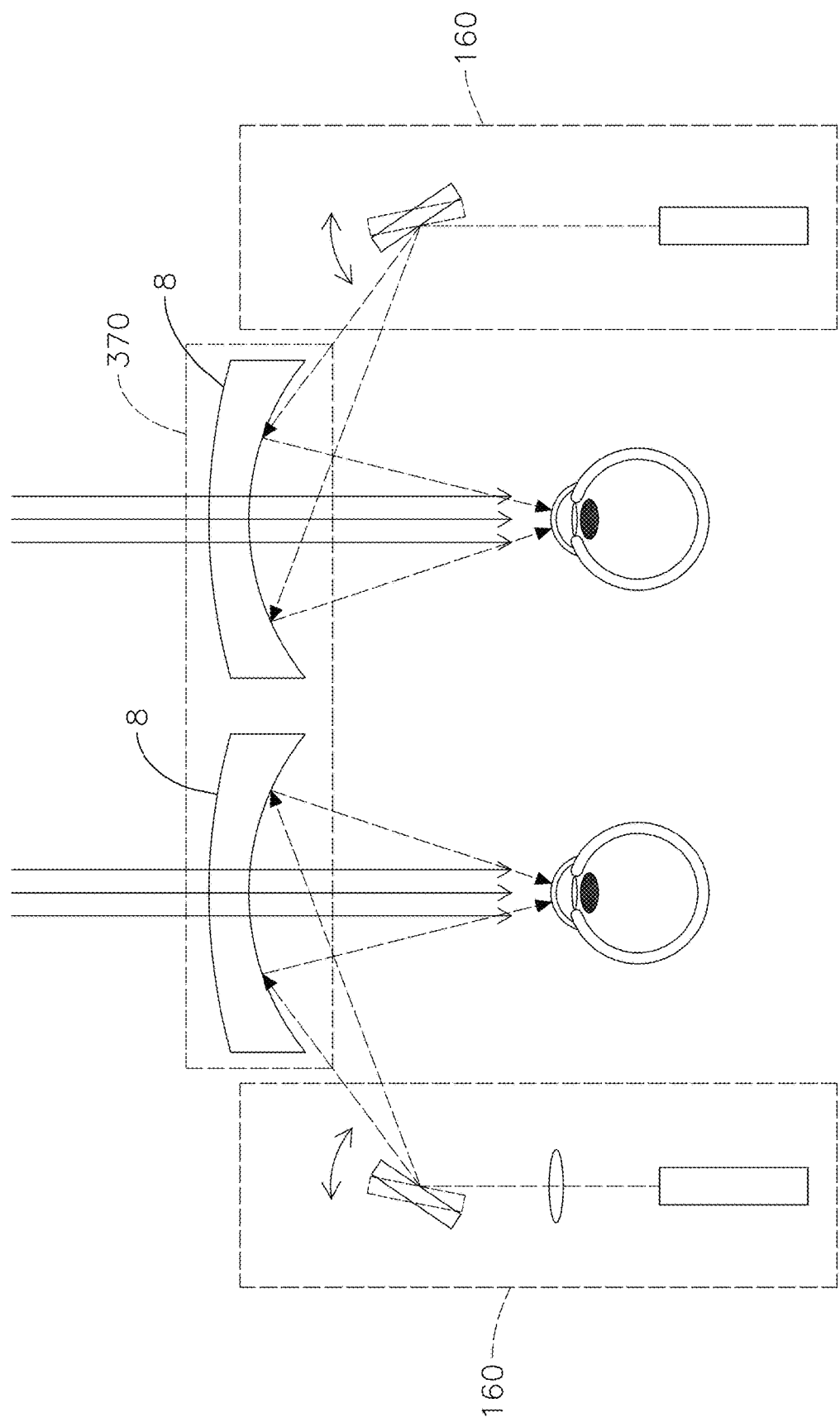
FIG. 3D is another schematic diagram illustrating an embodiment of the portable AR device.

FIG. 3B-3D show examples of a portable AR device 350 (head wearable device). With reference to FIG. 3B, the portable AR device 350 includes a real-time image module 370 and a virtual image module 360. The real-time image module 370 allows the real image of the surrounding and the image of the real object to enter the eyes of the user. In one embodiment of the present invention, the real-time image module 370 comprises a combiner of the portable augmented reality device. The real-time image module 370 may allow the real-time image from the surrounding or the image of the real object to enter the eyes of the viewer, while in the meantime, the real-time image module 370 may reflect the virtual image generated by the virtual image module 360 to the eyes of the viewer. With reference to FIG. 3C-3D, which illustrate two exemplary embodiments of the portable AR device; the portable AR device may comprise at least a virtual image module 160, and the real-time image module 370. The real-time image module 370 may comprise combiner 8, for allowing ambient light to enter the eyes of the viewer. In some embodiments, the combiner 8 may also reflect the image provided by the virtual image module 160 to the eyes of the viewer. In the present embodiment, the virtual image module 160 may comprise a laser emitter and other optical elements such as lenses and reflectors. The real-time image module 370 may or may not have the capability of magnifying the real-time image. In some embodiments, the real-time image module 370 may further comprise a beam splitter, as shown in FIG. 3C. In one embodiment, the real-time image module 370 does not have magnification function, the user can directly view the real object; thereby, the user can see the virtual object being directly superimposed on the real object.

Figure 4:
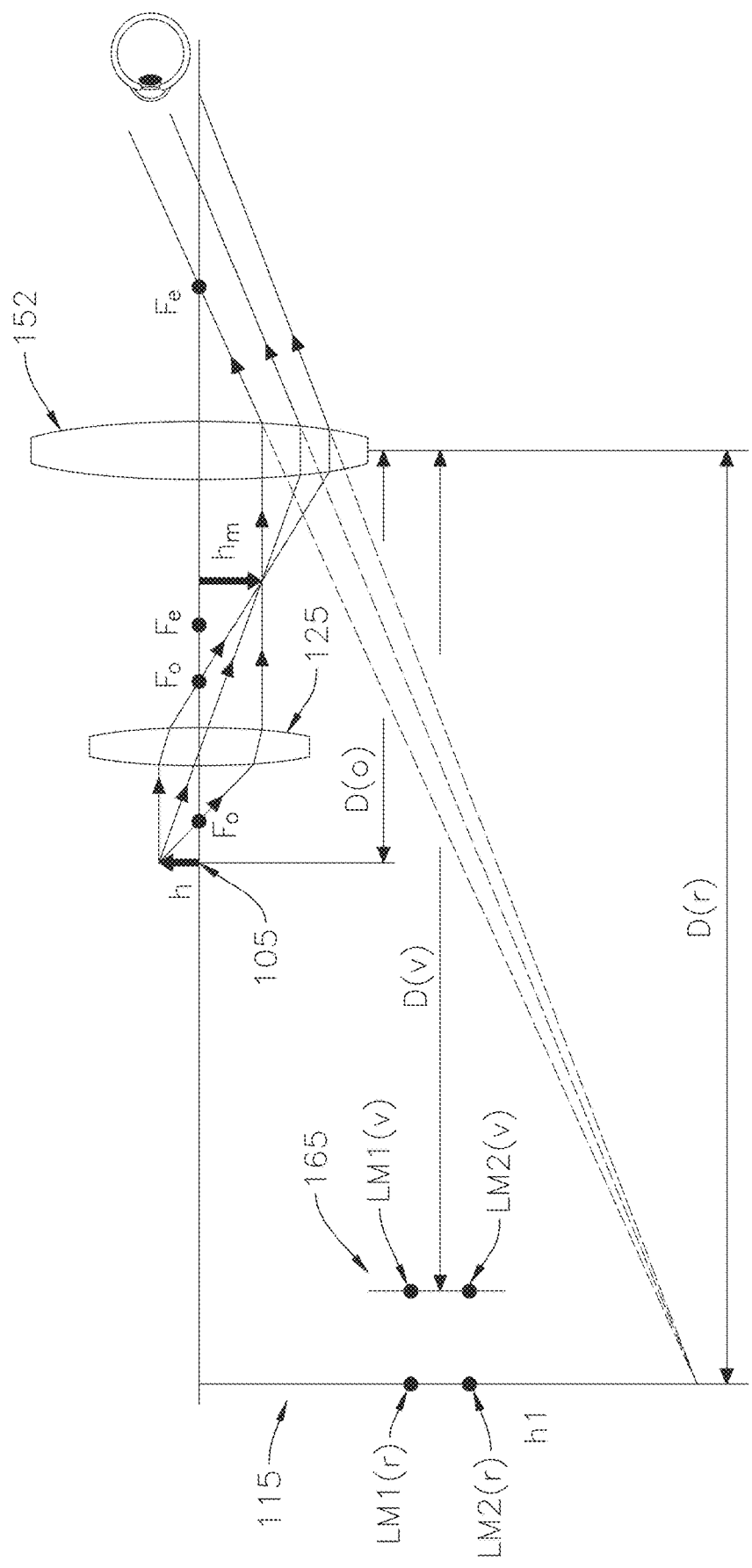
FIG. 4 is a schematic diagram illustrating an embodiment of the relationship between an object, a real-time image, and a virtual image in accordance with the present invention.

As shown in FIG. 4, the real object 105, the real-time image 115 generated by the real-time image module 110, and the virtual image 165 generated by the virtual image module 160, may have different locations and depths. In this embodiment, the virtual image 165 is a processed partial image of the real object 105. The virtual image module 160 may only generate the virtual image 165 for the field or area of interest of the real object. The image of the real object may be captured and processed, for example by an artificial intelligence (AI) module, for generating the virtual image within a very short time interval such as a second.

As described before, depending on the resolution, the real object 105, the real-time image 115, and the virtual image 165 may conceptually or actually comprise a large number of pixels, such as 921,600 pixels in a 1280×720 array. In this embodiment, the location and the depth of the real object 105, the real-time image 115, and the virtual image 165 are respectively represented by the location and depth of their corresponding first landmark. A depth is measured based on the distance between the eyepiece 152 and either the real object 105, or the real-time image 115, or the virtual image 165. Accordingly, as shown in FIG. 4, the real object 105 is located at the real object location L(o) and object depth D(o); the real-time image 115, a magnified image of the real object 105, is located at the second location L(r) and the second depth D(r); and the virtual image 165 is located at the first location L(v) and the first depth D(v). Depending on the optical features of the real-time image module, the depth of the real-time image 115 may be closer or farther to the viewer's eyes. In this embodiment, the depth of the real-time image D(r) is greater than the depth of the real object D(o). However, the depth of the real-time image D(r) may be less than or about the same as the depth of the real object D(o) in other embodiments. Then the virtual image 165 is generated by the virtual image module 160 at the depth D(v) which is closer to the eyepiece than the real-time image 115.

With the information of L(r) and D(r), as shown in FIG. 4, the virtual image module 160 of the system 100 may superimpose the virtual image on the real-time image by overlapping the corresponding first landmark LM1(v) on the virtual image with the first landmark LM1(r) on the real-time image. For a higher level of superimposition, the virtual image module 160 of the system 100 may further overlap the corresponding second landmark LM2(v) on the virtual image with the second landmark LM2(r) on the real-time image. In another embodiment where the superimposition goes beyond overlapping the landmarks with respect to their locations, the depth of the corresponding first landmark on the virtual image may be approximately the same as the depth of the first landmark on the real-time image. Similarly, the depth of the corresponding second landmark on the virtual image may be approximately the same as the depth of the second landmark on the real-time image. To precisely and completely superimpose a 3D virtual image on a 3D real-time image, in addition to the first landmark and the second landmark, the third landmark on the real-time image is selected. Then the virtual image module causes the location and the depth of the corresponding third landmark on the virtual image to be approximately the same as those of the third landmark on the real-time image.

Figure 5:
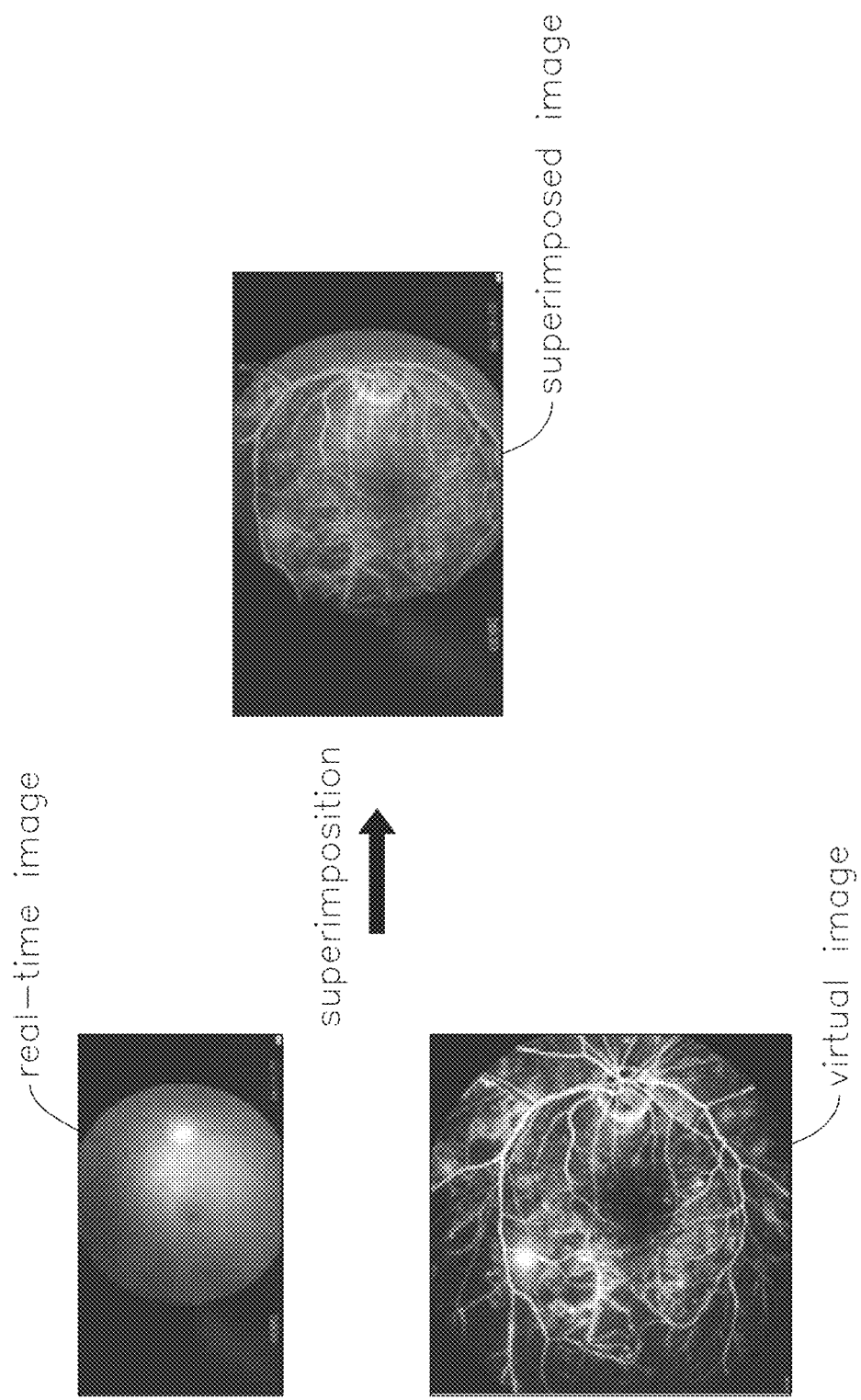
FIG. 5 are photos illustrating superimposition of a virtual image of a retina on a real-time image in accordance with the present invention.

FIG. 5 demonstrates three images-a real-time image of a patient's retina, a processed virtual image of the retina, and the superimposed image of both. In one embodiment, the angiographic image of the patent's retina is captured possibly by a slit-lamp biomicroscope and processed. Then the virtual image module 160 may use such processed image to project a virtual image superimposed on the real-time image of the patent's retina during a surgery to help identify and visualize the edges of choroidal neovascular membrane. The AR/MR microscope may greatly facilitate the diagnosis and treatment of various ophthalmic disorders and diseases.

Figure 6:
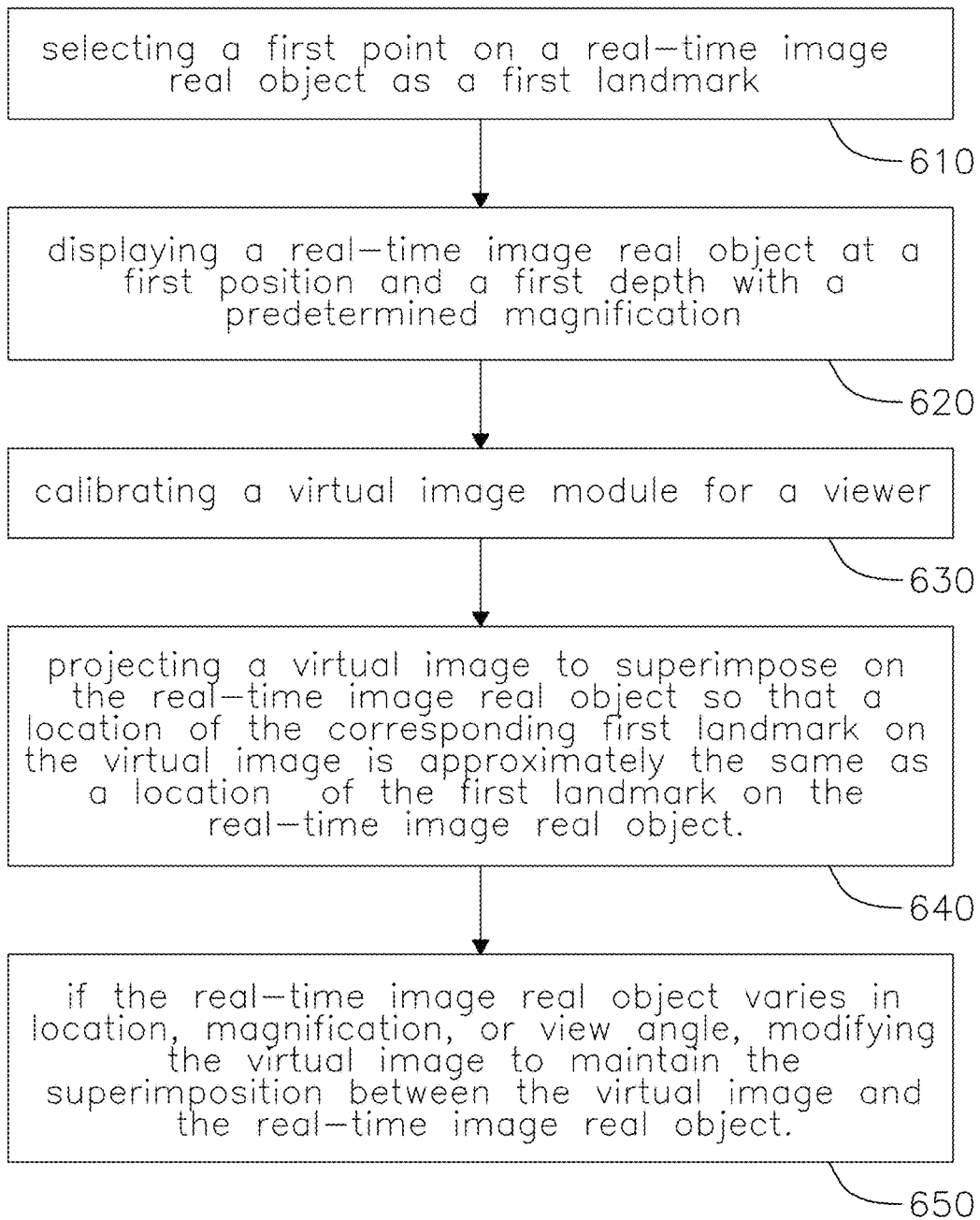
FIG. 6 is a flow chart illustrating an embodiment of processes for superimposing a virtual image on a real-time image in accordance with the present invention.

As shown in FIG. 6, the process of superimposing a virtual image on a real-time image or real object includes 4 steps. At step 610, a first point on a real-time image or real object is selected as a first landmark by a viewer, an expert, a computer, or the system 100. For example, a viewer may control a mouse to move a cursor or pointer viewable from the eyepieces to select the first landmark on the real-time image or real object. As described above, a landmark, including a first landmark, a second landmark, and a third landmark, is usually a unique point with a distinguishable feature that may be easily recognized by the viewer in the real-time image or real object, such as the central point, the intersection of two specific blood vessels. Landmarks may be defined either manually by experts or automatically by a computer program. There are three basic types of landmarks: anatomical landmarks, mathematical landmarks and pseudo-landmarks. An anatomical landmark is a biologically-meaningful point in an organism. Any anatomic feature—a fold, prominence, duct, vessel, etc.—consistently present in a tissue that serves to indicate a specific structure or position. Anatomic landmarks may be used by surgical pathologists for specimen orientation. Mathematical landmarks are points in a shape that are located according to some mathematical or geometrical property, for instance, a high curvature point or an extreme point. A computer program may determine mathematical landmarks used for an automatic pattern recognition. Pseudo-landmarks are constructed points located between anatomical or mathematical landmarks. A typical example is an equally spaced set of points between two anatomical landmarks to get more sample points from a shape. Pseudo-landmarks are useful during shape matching, when the matching process requires a large number of points. A landmark may be a pixel or comprise multiple pixels adjacent to each other.

At step 620, if the viewer is viewing the real-time image, a real-time image of the real object is displayed at a first location and a first depth with a predetermined magnification. If the viewer views the real object directly, the real object or the real-time image is not magnified. There are at least two types of real-time image. The first type of real-time image is generated by lights reflected or emitted from the real object, for example, the image observed by a microscope or a telescope. In this situation, the first location and the first depth may be determined by the optical features of the real-time image module. The viewer may observe the real-time image through the eyepieces. The second type of real-time image is generated by a display which receives an image of an object possibly taken by a camera in a real-time manner, for example, the image on a display from an endoscope, including gastroscope, colonoscope or proctoscope. The endoscope may have two image capturing devices positioned separately to take and generate a 3D image. The real-time image may be a two-dimensional (2D) image or a three-dimensional (3D) image. Step 610 and step 620 are exchangeable.

At step 630, the virtual image module is calibrated for a specific viewer. As described before, some physical characteristic of each viewer, such as interpupillary distance, may affect the location and depth of the virtual image the viewer perceives with the same right collimated light signals and the corresponding left collimated light signals. In one embodiment, the control module may adjust the virtual image signals based on the viewer's IPD so that the right collimated light signal generator 170 and the left collimated light signal generator 175 can project the light signals at appropriate locations and angles to assure the viewer perceives the virtual image at exactly the first location and the first depth.

At step 640, the virtual image module projects a virtual image by respectively projecting a right collimated light signal to a viewer's right eye and a corresponding left collimated light signal to a viewer's left eye for the viewer to perceive the virtual image at a first location and a first depth so that the corresponding first landmark on the virtual image overlaps the first landmark on the real-time image or the real object. In other words, the virtual image module projects a virtual image to superimpose on the real-time image or the real object. At least the location of the corresponding first landmark on the virtual image (first location) is approximately the same as the location of the first landmark on the real-time image or the real object (second location). In general, the virtual image is divided into multiple virtual binocular pixels, depending on the resolution, for example 921,600 virtual binocular pixels in a 1280×720 array. For each right collimated light signal and its corresponding left collimated light signal projected onto the viewer's retinas, the viewer perceives a virtual binocular pixel at a specific location and depth. The depth is related to the angle of the right collimated light signal and the corresponding left collimated light signal projected into the viewer's eye. More specifically, the perceived depth of a virtual binocular pixel corresponds to a depth location of a converging point of light path extensions of the right collimated light signal and the corresponding left collimated light signal. In other words, the perceived depth of a virtual binocular pixel is substantially equivalent to the depth location of a converging point of light path extensions of the right collimated light signal and the corresponding left collimated light signal. When the first landmark on the real-time image or the real object is at the second location and the second depth, the virtual binocular pixel of the corresponding first landmark on the virtual image is projected to be perceived by the viewer at the first location and the first depth. For an initial superimposition, the location of the corresponding first landmark on the virtual image (first location) is set to be approximately the same as the location of the first landmark on the real-time image or real object (second location) while their depths may be different. This superimposition can be achieved manually by the viewer or automatically by the system 100 using shape recognition technologies, including artificial intelligence (AI) algorithms. To further improve the superimposition, the first depth is set to be approximately the same as the second depth. In the case of superimposing the virtual image onto a real-time image, if the real-time image is magnified from the actual size of the real object, the virtual image needs to be magnified to the same extent for superimposition. Moreover, to further improve the superimposition, the view angle of the virtual image needs to match the view angle of the real-time image. The relationship between the light signals generated by the light signal generators and the depth perceived by the viewer is described in details below. In the case of superimposing the virtual image onto a real object, this can be achieved by configuring the converging point in proximity to one portion of the real object.

At step 650, if the real-time image varies in location, magnification, or view angle, the virtual image module modifies the virtual image to maintain the superimposition between the virtual image and the real-time image. By the same token, if the real object varies in location, or view angle, the virtual image module modifies the virtual image to maintain the superimposition between the virtual image and the real object. The variation of the location, magnification, and view angle of the real-time image or the real object may be caused by the viewer's operation or by the movement of the real object or the viewer. The system 100 constantly monitors the first location and first depth of the real-time image and the second location and the second depth of the virtual image. Once any variation of the real-time image or real object occurs, the virtual image module modifies the virtual image signal to maintain the superimposition between the virtual image and the real-time image or real object.

Figure 7:
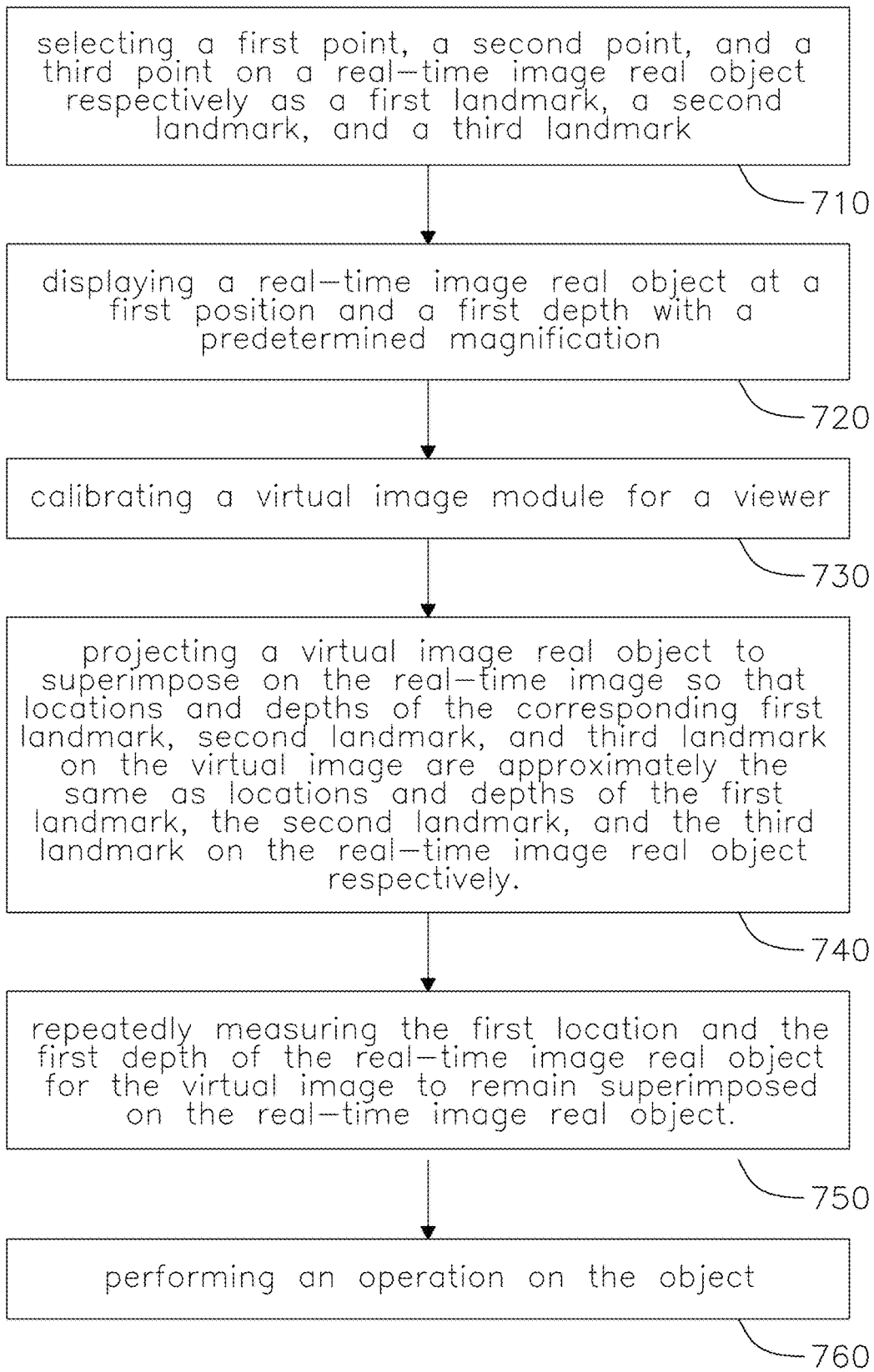
FIG. 7 is a flow chart illustrating another embodiment of processes for superimposing a virtual image on a real-time image in accordance with the present invention.

As shown in FIG. 7, an alternate process of superimposing a virtual image on a real-time image includes 6 steps. Some steps are the same or similar to those described in the prior embodiment shown in FIG. 6. Some steps are optional and can be further altered. At step 710, a first point, a second point, and a third point on a real-time image or real object are respectively selected as a first landmark, a second landmark, and a third landmark by a viewer, an expert, a computer, or the system 100. For the most precise superimposition, three landmarks are used here. Some surgeries, such as brain neurosurgery, requires very high level of accuracy, and thus three landmarks may be required to assure the virtual image is completely superimposed on the real-time image or real object. However, depending on the needs, the process may include two landmarks. Step 720 may be the same as step 620 and step 730 may be the same as step 630. Step 740 follows the same principles described for step 640. However, the locations and depths of the corresponding first landmark, second landmark, and third landmark on the virtual image are approximately the same as the locations and the depths of the first landmark, the second landmark, and the third landmark on the real-time image or the real object, respectively. At step 750, the second location and the second depth are repeatedly monitored or measured. The second location and the second depth may be calculated based on the location and depth of the real object relative to the real object measuring module (or the viewer) measured by the real object measuring module. As a result, the virtual image is able to remain superimposed on the real-time image or the real object. At step 760, the viewer, e.g. a surgeon, performs an operation on the real object by a laser or a scalpel at the spot of interest identified by the viewer.

Figure 8:
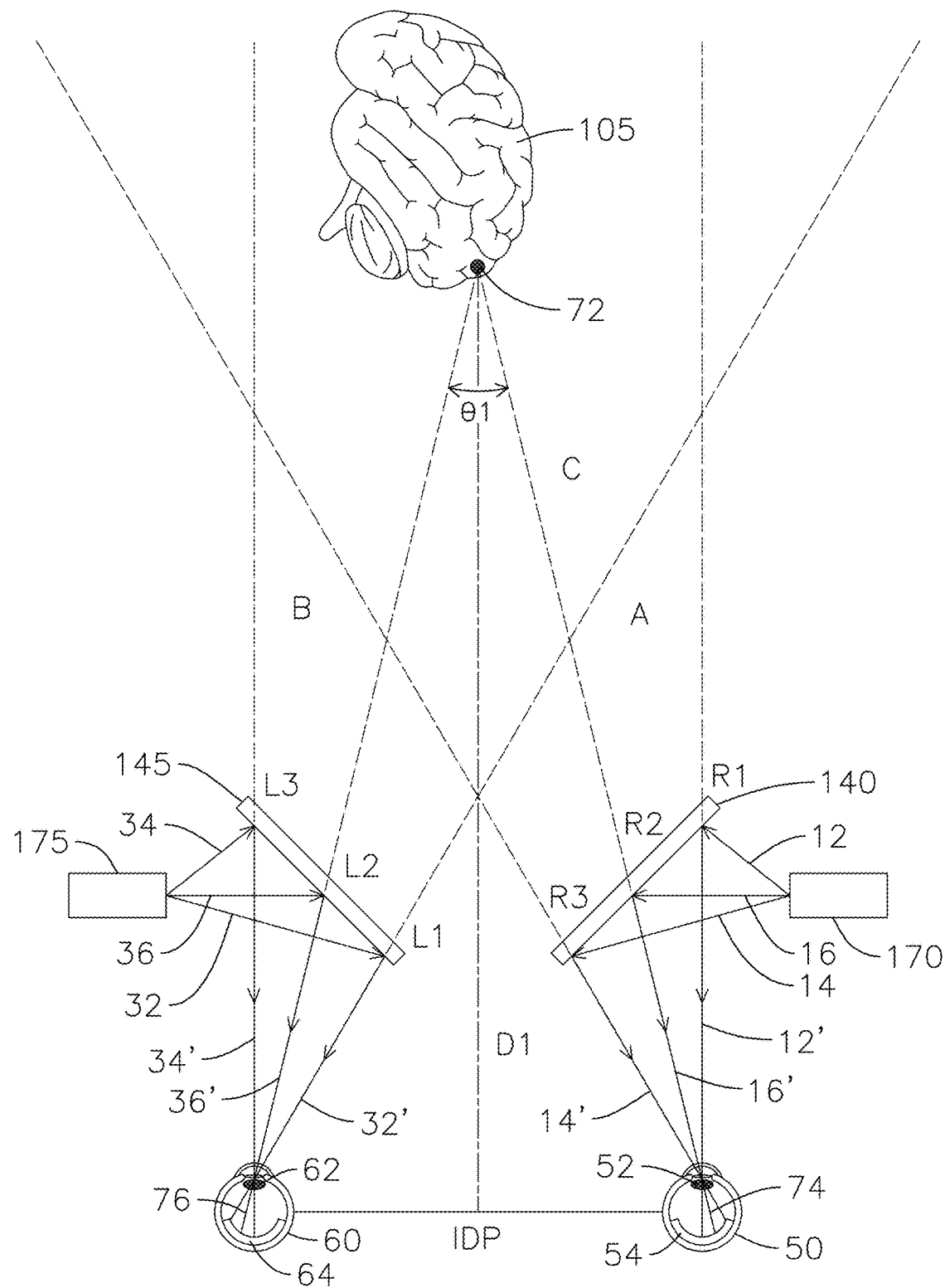
FIG. 8 is a schematic diagram illustrating an embodiment of a virtual image module in accordance with the present invention.

The virtual image module 160 and the method of generating a virtual image 165 at a first location and a first depth as well as the method of moving the virtual image as desired are discussed in details below. The PCT international application PCT/US20/59317, filed on Nov. 6, 2020, titled "SYSTEM AND METHOD FOR DISPLAYING AN OBJECT WITH DEPTHS" is incorporated herein by reference at its entirety. According to one embodiment, as shown in FIG. 8, the virtual image module 160 includes a right collimated light signal generator 170 to generate multiple right collimated light signals such as 12 for RLS_1, 14 for RLS_1 and 16 for RLS_3, a right beam splitter 140 to receive and redirect the multiple right collimated light signals towards the right retina 54 of a viewer, a left collimated light signal generator 175 to generate multiple left collimated light signals such as 32 for LLS_1, 34 for LLS_2, and 36 for LLS_3, and a left beam splitter 145 to receive and redirect the multiple left collimated light signals towards a left retina 64 of the viewer. The viewer has a right eye 50 containing a right pupil 52 and a right retina 54, and a left eye 60 containing a left pupil 62 and a left retina 64. The diameter of a human's pupil generally may range from 2 to 8 mm in part depending on the environmental lights. The normal pupil size in adults varies from 2 to 4 mm in diameter in bright light and from 4 to 8 mm in dark. The multiple right collimated light signals are redirected by the right beam splitter 140, pass the right pupil 52, and are eventually received by the right retina 54. The right collimated light signal RLS_1 is the light signal farthest to the right the viewer's right eye can see on a specific horizontal plan. The right collimated light signal RLS_2 is the light signal farthest to the left the viewer's right eye can see on the same horizontal plane. Upon receipt of the redirected right collimated light signals, the viewer would perceive multiple right pixels for the real object 105 in the area A bounded by the extensions of the redirected right collimated light signals RLS_1 and RLS_2. The area A is referred to as the field of view (FOV) for the right eye 50. Likewise, the multiple left collimated light signals are redirected by the left beam splitter 145, pass the center of the left pupil 62, and are eventually received by the left retina 64. The left collimated light signal LLS_1 is the light signal farthest to the right the viewer's left eye can see on the specific horizontal plan. The left collimated light signal LLS_2 is the light signal farthest to the left the viewer's left eye can see on the same horizontal plane. Upon receipt of the redirected left collimated light signals, the viewer would perceive multiple left pixels for the real object 105 in the area B bounded by the extensions of the redirected left collimated light signals LLS_1 and LLS_2. The area B is referred to as the field of view (FOV) for the left eye 60. When both multiple right pixels and left pixels are displayed in the area C which are overlapped by area A and area B, at least one right collimated light signal displaying one right pixel and a corresponding left collimated light signal displaying one left pixel are fused to display a virtual binocular pixel with a specific depth in the area C. The depth is related to an angle of the redirected right collimated light signal and the redirected left collimated light signal projected into the viewer's retinas. Such angle is also referred to as a convergence angle.

Figure 9:
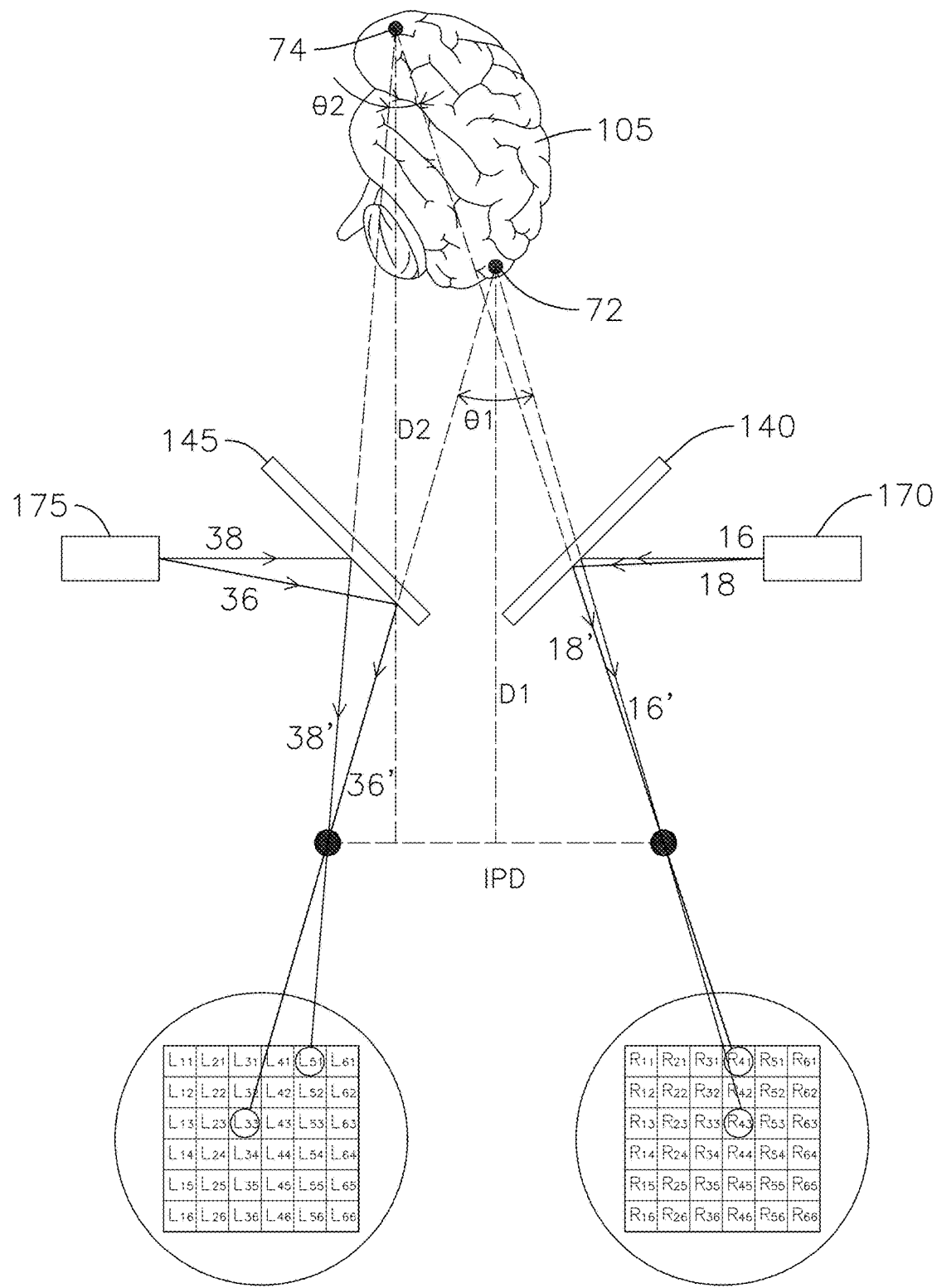
FIG. 9 is a schematic diagram illustrating a relationship between a virtual binocular pixel and the corresponding pair of the right pixel and left pixel in accordance with the present invention.

As shown in FIGS. 8 and 9, the viewer perceives a virtual image of the brain object 105 with multiple depths in the area C in front of the viewer. The image of the brain object 105 includes a first virtual binocular pixel 72 displayed at a first depth D1 and a second virtual binocular pixel 74 displayed at a second depth D2. The first angle between the light path extensions of the first redirected right collimated light signal 16' and the corresponding first redirected left collimated light signal 26' is Θ1. The first depth D1 is related to the first angle Θ1. In particular, the first depth of the first virtual binocular pixel of the real object 105 can be determined by the first angle Θ1 between the light path extensions of the first redirected right collimated light signal and the corresponding first redirected left collimated light signal. As a result, the first depth D1 of the first virtual binocular pixel 72 can be calculated approximately by the following formula:

$$\operatorname{Tan}\left(\frac{\theta}{2}\right) = \frac{IPD}{2D}$$

The distance between the right pupil 52 and the left pupil 62 is interpupillary distance (IPD). Similarly, the second angle between the second redirected right collimated light signal 18' and the corresponding second redirected left collimated light signal 38' is Θ2. The second depth D2 is related to the second angle Θ2. In particular, the second depth D2 of the second virtual binocular pixel of the real object 105 can be determined approximately by the second angle Θ2 between the light path extensions of the second redirected right collimated light signal and the corresponding second redirected left collimated light signal by the same formula. Since the second virtual binocular pixel 74 is perceived by the viewer to be further away from the viewer (i.e. with larger depth) than the first virtual binocular pixel 72, the second angle Θ2 is smaller than the first angle Θ1.

Furthermore, although the redirected right collimated light signal 16' for RLG_2 and the corresponding redirected left collimated light signal 36' for LLS_2 together display a first virtual binocular pixel 72 with the first depth D1. The redirected right collimated light signal 16' for RLG_2 may have the same or different view angle from the corresponding redirected left collimated light signal 36' for LLS_2. In other words, although the first angle Θ1 determines the depth of the first virtual binocular pixel, the redirected right collimated light signal 16' for RLG_2 may be or may not be a parallax of the corresponding redirected left collimated light signal 36' for LLS_2. Thus, the intensity of red, blue, and green (RBG) color and/or the brightness of the right collimated light signal and the left collimated light signal may be approximately the same or slightly different because of the shades, view angle, etc. to better present some 3D effects.

As described above, the multiple right collimated light signals are generated by the right collimated light signal generator, redirected by the right beam splitter, and then directly scanned onto the right retina to form a right retina image on the right retina. Likewise, the multiple left collimated light signals are generated by left collimated light signal generator, redirected by the left beam splitter, and then scanned onto the left retina to form a left retina image on the left retina. In an embodiment shown in FIG. 9, a right retina image 80 contains 36 right pixels in a 6×6 array and a left retina image 90 also contains 36 left pixels in a 6×6 array. In another embodiment, a right retina image 80 contains 921,600 right pixels in a 1280×720 array and a left retina image 90 also contains 921,600 left pixels in a 1280×720 array. The virtual image module 160 is configured to generate multiple right collimated light signals and corresponding multiple left collimated light signals which respectively form the right retina image on the right retina and left retina image on the left retina. As a result, the viewer perceives a virtual image with specific depths in the area C because of image fusion.

Notice that each left pixel or right pixel are form by one collimated light signal. Therefore, each left pixel or right pixel has a unique actual optical path in real space. This feature is different from the conventional waveguide-based head wearable display which each light signal for a pixel is not collimated and scattered.

With reference to FIG. 9, the first right collimated light signal 16 from the right collimated light signal generator 170 is received and reflected by the right beam splitter 140. The first redirected right collimated light signal 16', through the right pupil 52, arrives the right retina of the viewer to display the right pixel R43. The corresponding left collimated light signal 36 from the left collimated light signal generator 175 is received and reflected by the left beam splitter 145. The first redirected light signal 36', through the left pupil 62, arrives the left retina of the viewer to display the left retina pixel L33. As a result of image fusion, a viewer perceives the virtual image with multiple depths where the depths are determined by the angles of the multiple redirected right collimated light signals and the corresponding multiple redirected left collimated light signals. The angle between a redirected right collimated light signal and a corresponding left collimated light signal is determined by the relative horizontal distance of the right pixel and the left pixel. Thus, the depth of a virtual binocular pixel is inversely correlated to the relative horizontal distance between the right pixel and the corresponding left pixel forming the virtual binocular pixel. In other words, the deeper a virtual binocular pixel is perceived by the viewer, the smaller the relative horizontal distance at X axis between the right pixel and left pixel forming such a virtual binocular pixel is. For example, as shown in FIG. 9, the second virtual binocular pixel 74 is perceived by the viewer to have a larger depth (i.e. further away from the viewer) than the first virtual binocular pixel 72. Thus, the horizontal distance between the second right pixel and the second left pixel is smaller than the horizontal distance between the first right pixel and the first left pixel on the retina images. Specifically, the horizontal distance between the second right pixel R41 and the second left pixel L51 forming the second virtual binocular pixel is four-pixel long. However, the distance between the first right pixel R43 and the first left pixel L33 forming the first virtual binocular pixel is six-pixel long.

Figure 10:
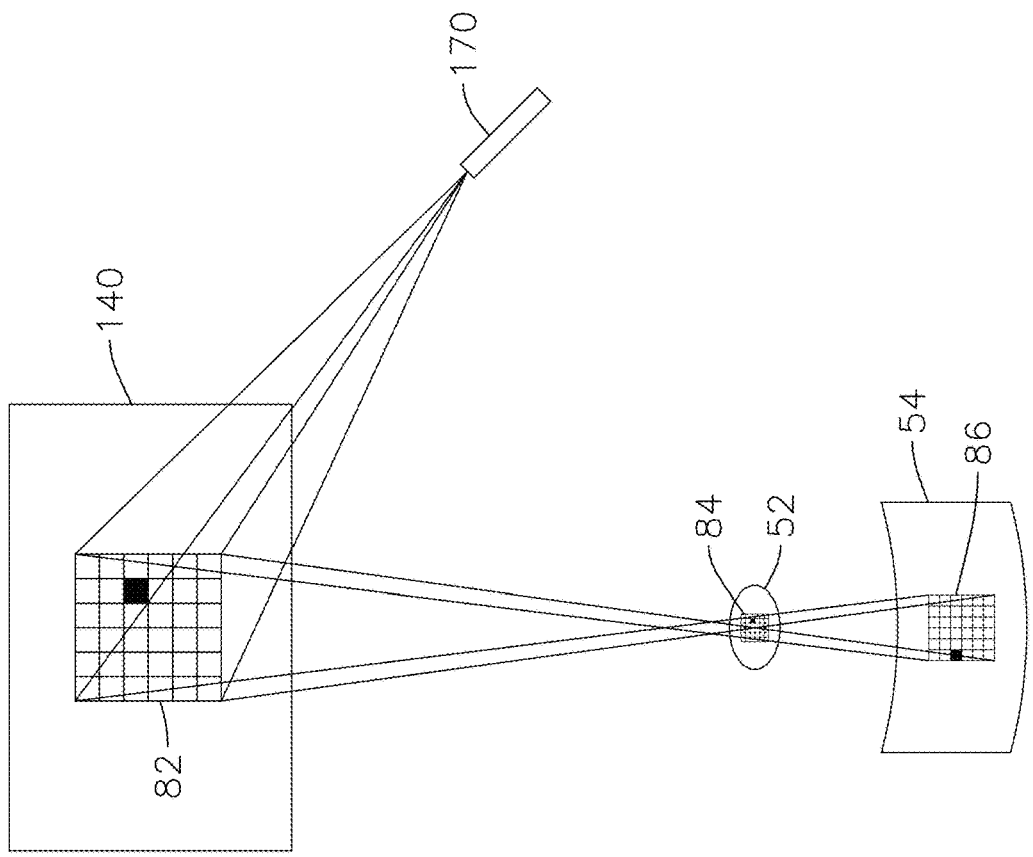
FIG. 10 is a schematic diagram illustrating the light path from a light signal generator to a beam splitter, and to a retina of a viewer in accordance with the present invention.
Figure 10:
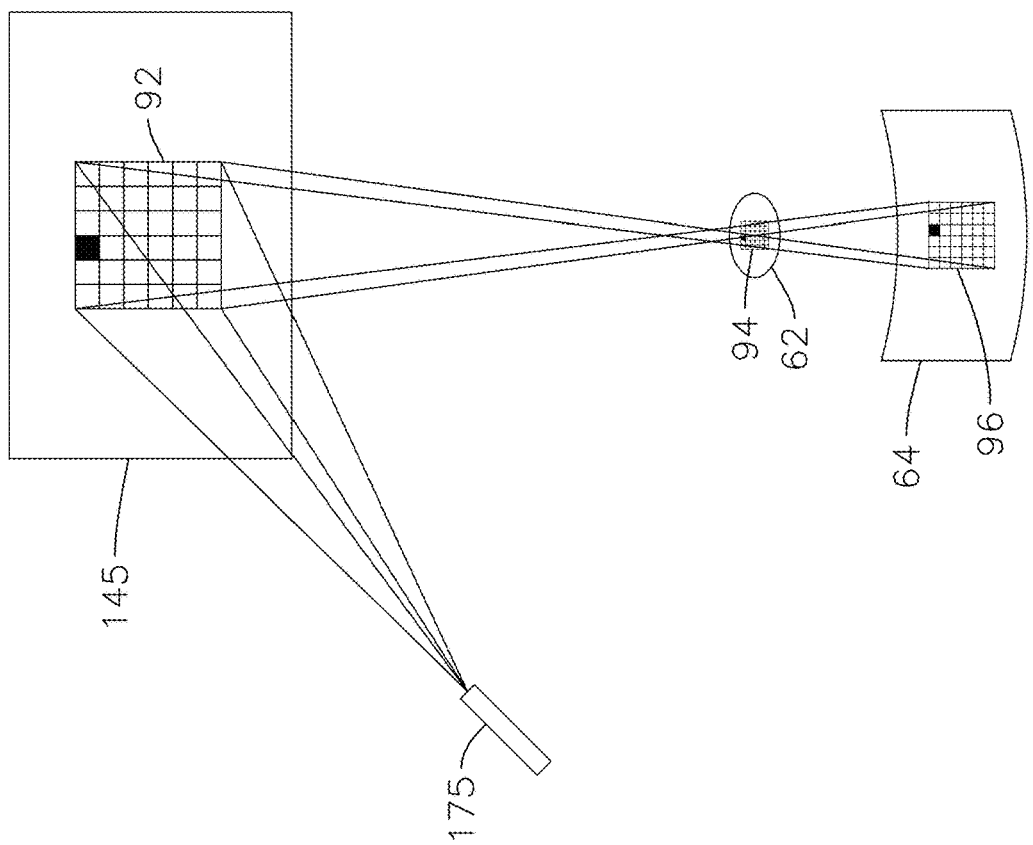

In one embodiment shown in FIG. 10, the light paths of multiple right collimated light signals and multiple left collimated light signals from light signal generators to retinas are illustrated. The multiple right collimated light signals generated from the right collimated light signal generator 170 are projected onto the right beam splitter 140 to form a right splitter image (RSI) 82. These multiple right collimated light signals are redirected by the right beam splitter 140 and converge into a small right pupil image (RPI) 84 to pass through the right pupil 52, and then eventually arrive the right retina 54 to form a right retina image (RRI) 86. Each of the RSI, RPI, and RRI comprises i×j pixels. Each right collimated light signal RLS (i,j) travels through the same corresponding pixels from RSI (i,j), to RPI (i,j), and then to RRI(x,y). For example RLS(5,3) travels from RSI(5,3), to RPI(5,3) and then to RRI(2,4). Likewise, the multiple left collimated light signals generated from the left collimated light signal generator 175 are projected onto the left beam splitter 145 to form a left splitter image (LSI) 92. These multiple left collimated light signals are redirected by the left beam splitter 145 and converge into a small left pupil image (LPI) 94 to pass through the left pupil 62, and then eventually arrive the left retina 64 to form a right retina image (LRI) 96. Each of the LSI, LPI, and LRI comprises i×j pixels. Each left collimated light signal LLS (i,j) travels through the same corresponding pixels from LCI(i,j), to LPI(i,j), and then to LRI(x,y). For example LLS(3,1) travels from LCI(3,1), to LPI(3,1) and then to LRI(4,6). The (0, 0) pixel is the top and left most pixel of each image. Pixels in the retina image is left-right inverted and top-bottom inverted to the corresponding pixels in the splitter image. Based on appropriate arrangements of the relative positions and angles of the light signal generators and beam splitters, each light signal has its own light path from a light signal generator to a retina. The combination of one right collimated light signal displaying one right pixel on the right retina and one corresponding left collimated light signal displaying one left pixel on the left retina forms a virtual binocular pixel with a specific depth perceived by a viewer. Thus, a virtual binocular pixel in the space can be represented by a pair of right retina pixel and left retina pixel or a pair of right splitter pixel and left splitter pixel.

A virtual image perceived by a viewer in area C includes multiple virtual binocular pixels. To precisely describe the location of a virtual binocular pixel in the space, each location in the space is provided a three-dimensional (3D) coordinate, for example XYZ coordinate. Other 3D coordinate system can be used in another embodiment. As a result, each virtual binocular pixel has a 3D coordinate-a horizontal direction, a vertical direction, and a depth direction. A horizontal direction (or X axis direction) is along the direction of interpupillary line. A vertical direction (or Y axis direction) is along the facial midline and perpendicular to the horizontal direction. A depth direction (or Z axis direction) is normal to the frontal plane and perpendicular to both the horizontal and vertical directions. The horizontal direction coordinate and vertical direction coordinate are collectively referred to as the location in the present invention.

Figure 11:
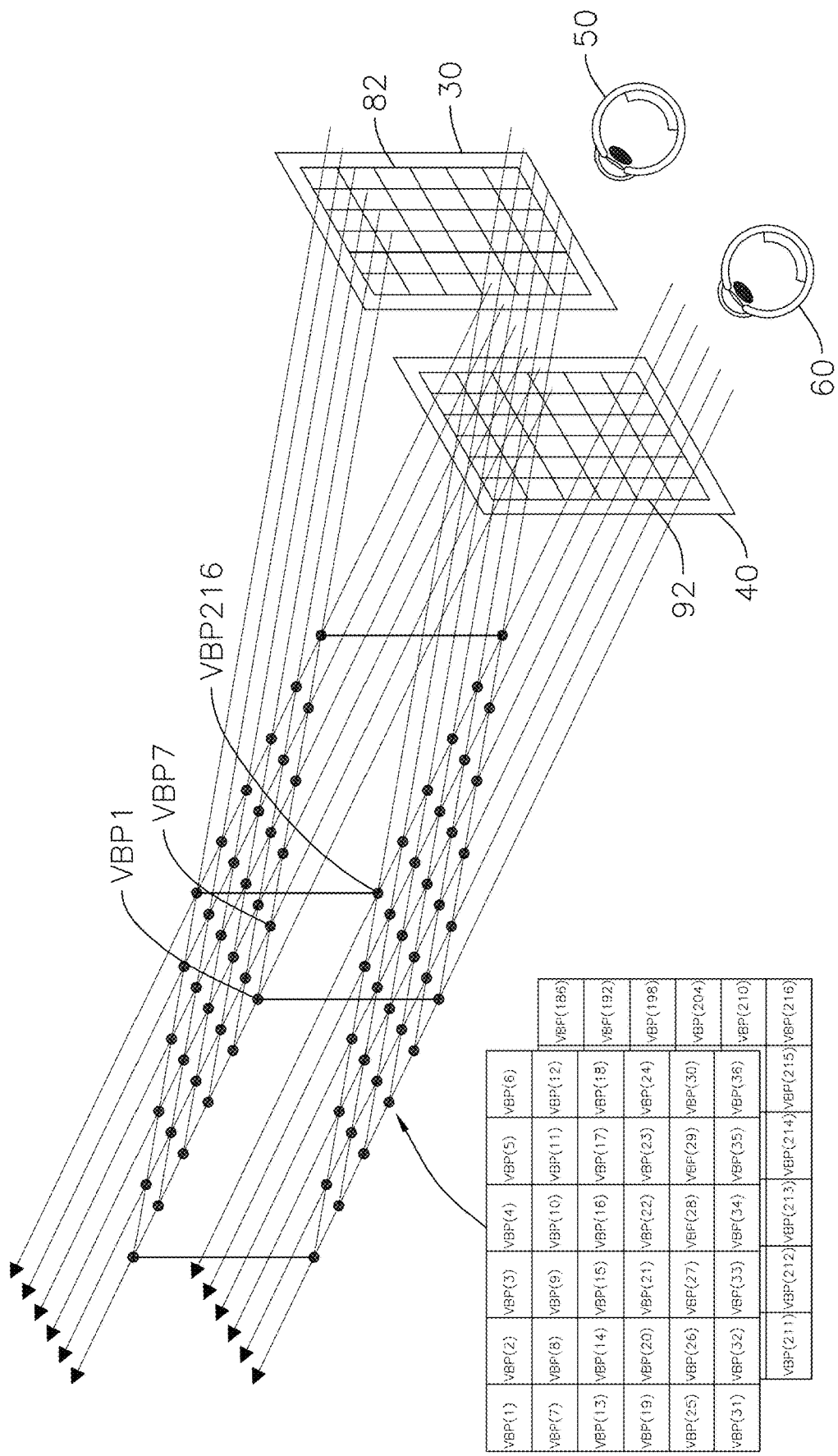
FIG. 11 is a schematic diagram illustrating the virtual binocular pixels formed by right collimated light signals and left collimated light signals in accordance with the present invention.

FIG. 11 illustrates the relationship between pixels in the right splitter image, pixels in the left splitter image, and the virtual binocular pixels. As described above, pixels in the right splitter image are one to one correspondence to pixels in the right retina image (right pixels). Pixels in the left splitter image are one to one correspondence to pixels in the left retina image (left pixels). However, pixels in the retina image is left-right inverted and top-bottom inverted to the corresponding pixels in the combiner image. However, if eyepieces 152, 154 are available in the system 100, the relationship between the pixels in the splitter image and the corresponding pixels in the retina image may be further modified by the optical features of the eyepieces. For a right retina image comprising 36 (6×6) right pixels and a left retina image comprising 36 (6×6) right pixels, there are 216 (6×6×6) virtual binocular pixels (shown as a dot) in the area C assuming all light signals are within FOV of both eyes of the viewer. The light path extension of one redirected right collimated light signal intersects the light path extension of each redirected left collimated light signal on the same row of the image. Likewise, the light path extension of one redirected left collimated light signal intersects the light path extension of each redirected right collimated light signal on the same row of the image. Thus, there are 36 (6×6) virtual binocular pixels on one layer and 6 layers in the space. There is usually a small angle between two adjacent lines representing light path extensions to intersect and form virtual binocular pixels although they are shown as parallel lines in the FIG. 11. A right pixel and a corresponding left pixel at approximately the same height of each retina (i.e. the same row of the right retina image and left retina image) tend to fuse earlier. As a result, right pixels are paired with left pixels at the same row of the retina image to form virtual binocular pixels.

As shown in FIG. 12, a look-up table is created to facilitate identifying the right pixel and left pixel pair for each virtual binocular pixel. For example, 216 virtual binocular pixels, numbering from 1 to 216, are formed by 36 (6×6) right pixels and 36 (6×6) left pixels. The first (1st) virtual binocular pixel VBP(1) represents the pair of right pixel RRI(1,1) and left pixel LRI(1,1). The second (2nd) virtual binocular pixel VBP(2) represents the pair of right pixel RRI(2,1) and left pixel LRI(1,1). The seventh (7th) virtual binocular pixel VBP(7) represents the pair of right pixel RRI(1,1) and left pixel LRI(2,1). The thirty-seventh (37th) virtual binocular pixel VBP(37) represents the pair of right pixel RRI(1,2) and left pixel LRI(1,2). The two hundred and sixteenth (216th) virtual binocular pixel VBP(216) represents the pair of right pixel RRI(6,6) and left pixel LRI(6,6). Thus, in order to display a specific virtual binocular pixel of a virtual image in the space for the viewer, it is determined which pair of the right pixel and left pixel can be used for generating the corresponding right collimated light signal and left collimated light signal. In addition, each row of a virtual binocular pixel on the look-up table includes a pointer which leads to a memory address that stores the perceived depth (2) of the VBP and the perceived position (x,y) of the VBP. Additional information, such as scale of size, number of overlapping objects, and depth in sequence depth etc., can also be stored for the VBP. Scale of size may be the relative size information of a specific VBP compared against a standard VBP. For example, the scale of size may be set to be 1 when the virtual image is displayed at a standard VBP that is 1 m in front of the viewer. As a result, the scale of size may be set to be 1.2 for a specific VBP that is 90 cm in front of the viewer. Likewise, when the scale of size may be set to be 0.8 for a specific VBP that is 1.5 m in front of the viewer. The scale of size can be used to determine the size of the virtual image for displaying when the virtual image is moved from a first depth to a second depth. Scale of size may be the magnification in the present invention. The number of overlapping objects is the number of objects that are overlapped with one another so that one object is completely or partially hidden behind another object. The depth in sequence provides information about sequence of depths of various overlapping images. For example, 3 images overlapping with each other. The depth in sequence of the first image in the front may be set to be 1 and the depth in sequence of the second image hidden behind the first image may be set to be 2. The number of overlapping images and the depth in sequence may be used to determine which and what portion of the images need to be displayed when various overlapping images are in moving.

The look up table may be created by the following processes. At the first step, obtain an individual virtual map based on his/her IPD, created by the virtual image module during initiation or calibration, which specify the boundary of the area C where the viewer can perceive a virtual image with depths because of the fusion of right retina image and left retina image. At the second step, for each depth at Z axis direction (each point at Z-coordinate), calculate the convergence angle to identify the pair of right pixel and left pixel respectively on the right retina image and the left retina image regardless of the X-coordinate and Y-coordinate location. At the third step, move the pair of right pixel and left pixel along X axis direction to identify the X-coordinate and Z-coordinate of each pair of right pixel and left pixel at a specific depth regardless of the Y-coordinate location. At the fourth step, move the pair of right pixel and left pixel along Y axis direction to determine the Y-coordinate of each pair of right pixel and left pixel. As a result, the 3D coordinate system such as XYZ of each pair of right pixel and left pixel respectively on the right retina image and the left retina image can be determined to create the look up table. In addition, the third step and the fourth step are exchangeable.

The light signal generator 170 and 175 may use laser, light emitting diode ("LED") including mini and micro LED, organic light emitting diode ("OLED"), or superluminescent diode ("SLD"), LCOS (Liquid Crystal on Silicon), liquid crystal display ("LCD"), or any combination thereof as its light source. In one embodiment, the light signal generator 170 and 175 is a laser beam scanning projector (LBS projector) which may comprise the light source including a red color light laser, a green color light laser, and a blue color light laser, a light color modifier, such as Dichroic combiner and Polarizing combiner, and a two dimensional (2D) adjustable reflector, such as a 2D electromechanical system ("MEMS") mirror. The 2D adjustable reflector can be replaced by two one dimensional (1D) reflector, such as two 1D MEMS mirror. The LBS projector sequentially generates and scans light signals one by one to form a 2D image at a predetermined resolution, for example 1280×720 pixels per frame. Thus, one light signal for one pixel is generated and projected at a time towards the beam splitter 140, 145. For a viewer to see such a 2D image from one eye, the LBS projector has to sequentially generate light signals for each pixel, for example 1280×720 light signals, within the time period of persistence of vision, for example 1/18 second. Thus, the time duration of each light signal is about 60.28 nanosecond.

In another embodiment, the light signal generator 170 and 175 may be a digital light processing projector ("DLP projector") which can generate a 2D color image at one time. Texas Instrument's DLP technology is one of several technologies that can be used to manufacture the DLP projector. The whole 2D color image frame, which for example may comprise 1280×720 pixels, is simultaneously projected towards the splitters 140 and 145.

The beam splitter 140, 145 receives and redirects multiple light signals generated by the light signal generator 170, 175. In one embodiment, the beam splitter 140, 145 reflects the multiple light signals so that the redirected light signals are on the same side of the beam splitter 140, 145 as the incident light signals. In another embodiment, the beam splitter 140, 145 refracts the multiple light signals so that the redirected light signals are on the different side of the beam splitter 140, 145 from the incident light signals. When the beam splitter 140, 145 functions as a refractor. The reflection ratio can vary widely, such as 20%-80%, in part depending on the power of the light signal generator. People with ordinary skill in the art know how to determine the appropriate reflection ratio based on characteristics of the light signal generators and the splitters. Besides, in one embodiment, the beam splitter 140, 145 is optically transparent to the ambient (environmental) lights from the opposite side of the incident light signals so that the viewer can observe the real-time image at the same time. The degree of transparency can vary widely depending on the application. For AR/MR application, the transparency is preferred to be more than 50%, such as about 75% in one embodiment. In addition to redirecting the light signals, the focus adjustment unit 182, 187 may converge the multiple light signals so that they can pass through the pupils and arrive the retinas of the viewer's both eyes.

The beam splitter 140, 145 may be made of glasses or plastic materials like lens, coated with certain materials such as metals to make it partially transparent and partially reflective. One advantage of using a reflective splitter instead of a wave guide in the prior art for directing light signals to the viewer's eyes is to eliminate the problem of undesirable diffraction effects, such as multiple shadows, color displacement . . . etc.

Figure 13:
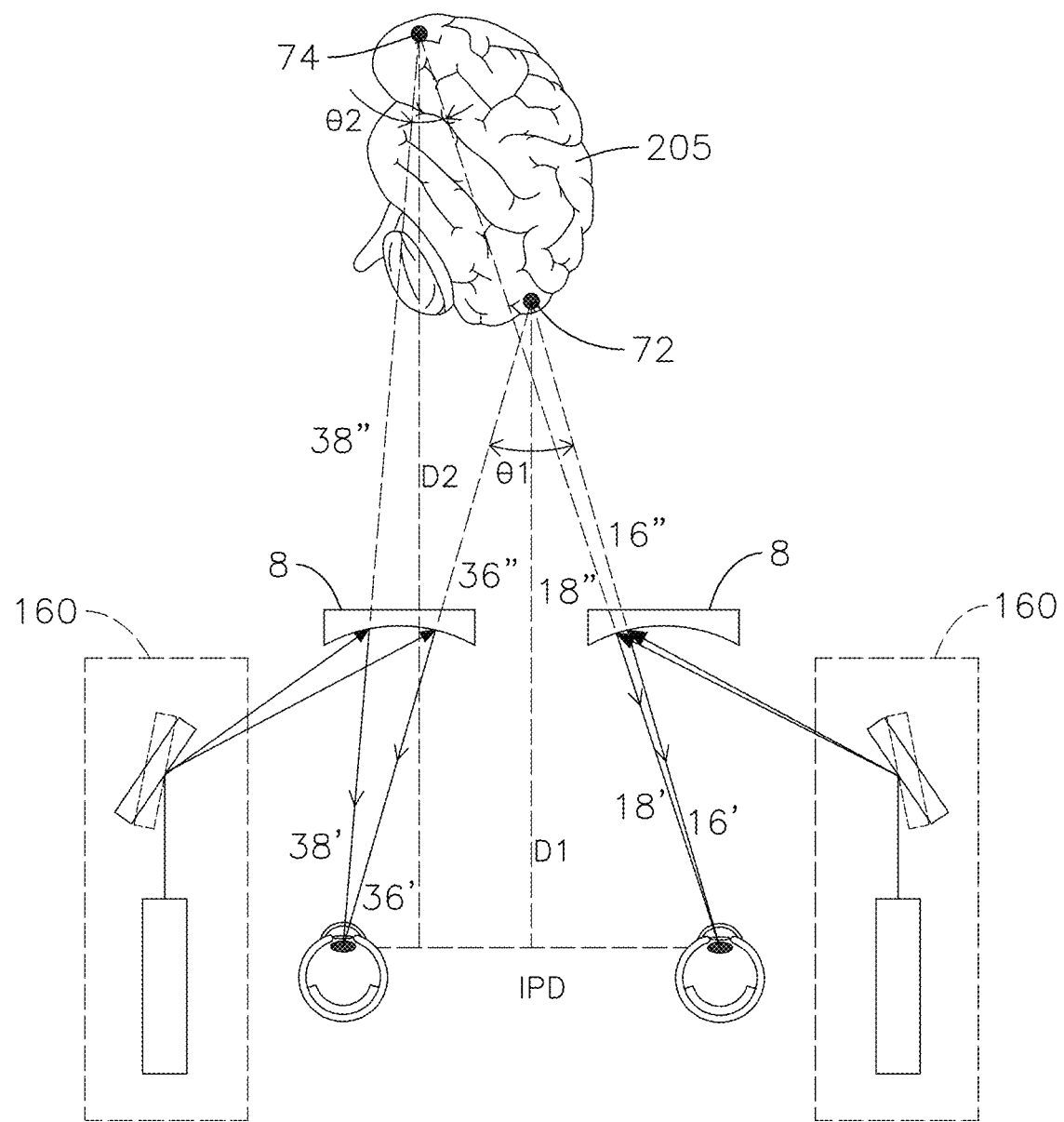
FIG. 13 is a schematic diagram illustrating the method for superimposing virtual binocular pixels onto a real object in accordance with the present invention.

With reference to FIG. 13, which illustrates an exemplary method for displaying a superimposed virtual image on a real object 205, the virtual image mentioned in the present invention is composed of a plurality of virtual binocular pixels, with each virtual binocular pixel formed by a pair consisting of a right pixel and a left pixel. In FIG. 13, only a first virtual binocular pixel 72 and a second virtual binocular pixel 74 are shown for simplicity. These two virtual binocular pixels are superimposed on the real object 205; the first virtual binocular pixel 72 is superimposed on a first portion of the real object 205 that has a depth D1 (both the first virtual binocular pixel 72 and the first portion of the real object 205 has similar depth D1) away from the viewer or the real object measuring module), the second virtual binocular pixel 74 is superimposed on a second portion of the real object 205 that has a depth D2 (both the second virtual binocular pixel 74 and the second portion of the real object 205 has similar depth D2) away from the viewer or the real object measuring module. As described above, the depth of a virtual binocular pixel is determined by the convergence angle between the optical path extensions of the collimated light signals composing the right and left pixels. And the depth of the virtual binocular pixel is determined by the depth coordinate of the convergence point of the optical path extensions of the collimated light signals composing the right and left pixels. With the use of a collimated light source, the visual axes of the two eyes may substantially align with the optical path (or optical path extensions) of the right pixel and the left pixel when the viewer fixates on the virtual binocular pixel, causing the fixation location of the eyes to coincide with the location of the rendered (converging point of the optical path extensions of the collimated light signals) virtual binocular pixel in real space. This feature is crucial because it eliminates focal rivalry and vergence-accommodation conflict. Furthermore, this feature can be applied to superimposing a virtual binocular pixel onto a real object in real space.

In the present invention, the right pixel is rendered by a right collimated light signal, and the left pixel is rendered by a left collimated light signal. The fusion of the right pixel and the left pixel creates a virtual binocular pixel. Each virtual binocular pixel of a virtual image may have a different depth. The depth of each virtual binocular pixel perceived by the viewer is modified by changing the convergence angle between the light path extensions (16", 18", 36", and 38" in FIG. 13) of the right collimated light signal and the corresponding left collimated light signal projected into the viewer's eyes, based on an interpupillary distance, as mentioned earlier. The perceived depth of the virtual binocular pixel corresponds to a depth location (or coordinate) of the converging point of the light path extensions of the right collimated light signal and the corresponding left collimated light signal. More specifically, in theory, the perceived depth location of the virtual binocular pixel is the depth location (or coordinate) of the converging point of the light path extensions of the right collimated light signal and the corresponding left collimated light signal. However, due to various variations and factors (e.g., mechanical dimension variations, human physiological factors, etc.), the perceived depth (coordinate) is substantially the same as, but not exactly the same as, the depth (coordinate) of the converging point in real practice. Regardless, since the depth and position of the virtual binocular image perceived by the viewer in real space are determined by the location of the converging point in real space, superimposing a virtual binocular pixel onto a real object in real space can be achieved by configuring the projection angle of the right and left collimated light signals such that the converging point is in proximity to a target portion of the real object, or preferably, as close to the superimposing target location on the real object as possible.

The present invention is especially advantageous relative to the prior art because of its ability to render different depths for every binocular pixel of a virtual image. Since the surface of a real object may have a contour, it can be difficult to superimpose a virtual image onto the real object perfectly with previous 3D rendering technologies, which are unable to configure the depth of every single binocular pixel to fit the contour of the real object. However, with the present invention, the depth of every virtual binocular pixel can be configured to be close to a target portion of the real object by adjusting the converging point of the collimated light signals (left and right) to be as close to the real object (e.g., the surface of the real object) as possible. Furthermore, no focal rivalry will occur when the viewer observes the real object and the superimposed virtual image simultaneously, this is because the converging point of the optical path extension of the binocular pixel is on the real object, and the location of the converging point of the visual axes of the viewer is also the same as the converging point of the optical path extension of the binocular pixel.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter. Thus, it is intended that the present invention covers modifications and variations that come within the scope of the appended claims and their equivalents.

What is claimed is:

1. A virtual image module for generating a virtual image with depth, comprising:
   a right collimated light signal generator for generating a right collimated light signal which is directed towards one retina of a viewer;
   a left collimated light signal generator for generating a left collimated light signal corresponding to the right collimated light signal which is directed towards the other retina of the viewer;
   wherein the right collimated light signal and the left collimated light signal form a binocular pixel of a virtual image with a first depth, the first depth which the viewer perceives is modified by changing a convergence angle between light path extensions of the right collimated light signal and the corresponding left collimated light signal projected into the viewer's eyes based on an interpupillary distance, the first depth corresponds to a depth location of a converging point of light path extensions of the right collimated light signal and the corresponding left collimated light signal;
   wherein the virtual image is augmented and superimposed to a real object having a second depth by configuring the converging point in proximity to one portion of the real object,
   wherein the first depth and a magnification of the virtual image are altered according to the second depth,
   wherein the virtual image module is inclusive in a portable augmented reality device,
   wherein the portable augmented reality device comprises a real-time image module, the real-time image module comprises a combiner of the portable augmented reality device.

2. The virtual image module for generating a virtual image with depth of claim 1, wherein the first depth and the magnification of the virtual image are altered according to the second depth.

3. The virtual image module for generating a virtual image with depth of claim 1, wherein the virtual image is a photograph, a magnetic resonance image, an x-ray image, a computed tomography, and an optical coherence tomography of a body organ or tissue provided by the virtual image module.

4. The virtual image module for generating a virtual image with depth of claim 3, wherein the virtual image is marked with a location, a guidance, an instruction, or a navigation to perform a surgery.

5. The virtual image module for generating a virtual image with depth of claim 2, wherein a first point on the real object is selected as a first landmark for superimposing the virtual image on the real object by overlapping a corresponding first landmark on the virtual image on the first landmark on the real object.

6. The virtual image module for generating a virtual image with depth of claim 5, wherein a second point on the real object is selected as a second landmark for superimposing the virtual image on the real object by overlapping a corresponding second landmark on the virtual image on the second landmark on the real object.

7. The virtual image module for generating a virtual image with depth of claim 1, wherein the virtual image module further comprises a control module to process the right collimated light signal and the corresponding left collimated light signal so that the virtual image is modified to be superimposed on the real object based on a view angle, and a location of the real object.

8. The virtual image module for generating a virtual image with depth of claim 1, further comprising:
   an object measuring module configured to measure a location and the second depth of a portion of the real object.

\* \* \* \* \*